(12) United States Patent
Udagawa et al.

(10) Patent No.: US 6,514,739 B1
(45) Date of Patent: Feb. 4, 2003

(54) LYSOPHOSPHOLIPASE

(76) Inventors: Hiroaki Udagawa, 1-2-5, Isezaki-cho Naka-ku, Yokohama-shi (JP), 231-45; Torben Peter Frandsen, Alhambravej 22, 1. TH, DK-1826 Frederiksberg C (DK); Tom Anton Busk Nielsen, 186-2 Chigusacho, Hanamigawa-ku, Chiba (JP), 262-0012; Markus Sakari Kauppinen, Norskekrogen 12, DK-2765 Smørum (DK); Søren Christensen, Korsørgrade 6, 3 th., DK-2100 Copenhagen Ø (DK)

( * ) Notice: Subject to any disclaimer, the term of this patent is extended or adjusted under 35 U.S.C. 154(b) by 81 days.

(21) Appl. No.: 09/687,538

(22) Filed: Oct. 13, 2000

Related U.S. Application Data
(60) Provisional application No. 60/160,572, filed on Oct. 20, 1999.

(30) Foreign Application Priority Data

Oct. 14, 1999 (DK) .......................................... 1999 01473

(51) Int. Cl.[7] .................................................. C12N 9/18
(52) U.S. Cl. ........................ 435/197; 435/196; 435/266; 435/267
(58) Field of Search ............................ 435/196, 252.33, 435/197; 536/23.2

(56) References Cited

U.S. PATENT DOCUMENTS

| | | | |
|---|---|---|---|
| 5,965,422 A | 10/1999 | Loffler et al. | ................ 435/198 |
| 6,146,869 A | 11/2000 | Harris et al. | ................ 435/198 |

FOREIGN PATENT DOCUMENTS

| | | |
|---|---|---|
| EP | 0 219 269 | 4/1987 |
| EP | 0 808 903 | 11/1997 |
| JP | 10-155493 | 6/1998 |
| WO | WO 98/31790 | 7/1998 |

OTHER PUBLICATIONS

Masuda et al., Eur. J. Biochem., vol. 202, pp. 783–787 (1991).

Process Biochemistry, Mustranata et al., pp. 393–401, 1995.

*Primary Examiner*—Nashaat T. Nashed
(74) *Attorney, Agent, or Firm*—Jason I Garbell

(57) ABSTRACT

The inventors have isolated lysophospholipases from Aspergillus (*A. niger* and *A. oryzae*) having molecular masses of about 68 kDa and amino acid sequences of 600–604 amino acid residues. The novel lysophospholipases have only a limited homology to known amino acid sequences. The inventors also isolated genes encoding the novel enzymes and cloned them into *E. coli* strains.

13 Claims, No Drawings

SEQUENCE LISTING

```
<160> NUMBER OF SEQ ID NOS: 19

<210> SEQ ID NO 1
<211> LENGTH: 1923
<212> TYPE: DNA
<213> ORGANISM: Aspergillus niger
<220> FEATURE:
<221> NAME/KEY: CDS
<222> LOCATION: (1)..(1920)
<223> OTHER INFORMATION:
<221> NAME/KEY: sig_peptide
<222> LOCATION: (1)..(63)
<223> OTHER INFORMATION:
<221> NAME/KEY: mat_peptide
<222> LOCATION: (109)..()
<223> OTHER INFORMATION:

<400> SEQUENCE: 1 atg aag ttc aat gca ctc tta acg acc ctc gcg gcg ctg ggg tat atc      48
Met Lys Phe Asn Ala Leu Leu Thr Thr Leu Ala Ala Leu Gly Tyr Ile
 -35             -30                 -25
```

-continued

| | | | | | | | | | | | | |
|---|---|---|---|---|---|---|---|---|---|---|---|---|
| caa | gga | ggc | gcc | gcg | gtt | cct | aca | acc | gtc | gac | ctc | aca | tat | gca | gac | 96 |
| Gln | Gly | Gly | Ala | Ala | Val | Pro | Thr | Thr | Val | Asp | Leu | Thr | Tyr | Ala | Asp | |
| -20 | | | | -15 | | | | -10 | | | | | | -5 | | |

```
caa gga ggc gcc gcg gtt cct aca acc gtc gac ctc aca tat gca gac        96
Gln Gly Gly Ala Ala Val Pro Thr Thr Val Asp Leu Thr Tyr Ala Asp
-20              -15              -10                      -5 ata tca cct cgc gca ctg gat aat gcc cct gat ggt tat acc ccg agc       144
Ile Ser Pro Arg Ala Leu Asp Asn Ala Pro Asp Gly Tyr Thr Pro Ser
         -1  1              5                        10 aat gta tcc tgt cct gca aac aga ccg acg att cgc agc gcg tca acc       192
Asn Val Ser Cys Pro Ala Asn Arg Pro Thr Ile Arg Ser Ala Ser Thr
         15              20              25 ctg tca tcg aac gag acg gca tgg gtg gac gtc cgg cgt aag cag act       240
Leu Ser Ser Asn Glu Thr Ala Trp Val Asp Val Arg Arg Lys Gln Thr
     30              35              40 gtc tca gcg atg aaa gac ctt ttc ggc cat atc aac atg agc tca ttt       288
Val Ser Ala Met Lys Asp Leu Phe Gly His Ile Asn Met Ser Ser Phe
45              50              55                          60 gac gct att tcg tac atc aac agc cat tca tca aat atc acc aac ata       336
Asp Ala Ile Ser Tyr Ile Asn Ser His Ser Ser Asn Ile Thr Asn Ile
             65              70              75 ccc aac atc ggt att gcc gtg tcc ggc ggt ggc tac aga gcc ctg acc       384
Pro Asn Ile Gly Ile Ala Val Ser Gly Gly Gly Tyr Arg Ala Leu Thr
         80              85              90 aac ggc gcg gga gca ctc aag gca ttc gac agt cga acg gaa aac tca       432
Asn Gly Ala Gly Ala Leu Lys Ala Phe Asp Ser Arg Thr Glu Asn Ser
         95              100             105 acc cat aat gga cag ctc ggt ggt ctt ctg cag tca gcc aca tac ctg       480
Thr His Asn Gly Gln Leu Gly Gly Leu Leu Gln Ser Ala Thr Tyr Leu
110             115             120 tcc ggt ctc tcc gga ggt ggc tgg ctc ctg ggc tca atc tac atc aac       528
Ser Gly Leu Ser Gly Gly Gly Trp Leu Leu Gly Ser Ile Tyr Ile Asn
125             130             135                         140 aac ttc acc acc gtc tcc aat ctg caa acc tac aaa gag ggc gaa gtc       576
Asn Phe Thr Thr Val Ser Asn Leu Gln Thr Tyr Lys Glu Gly Glu Val
             145             150             155 tgg cag ttc cag aat tca atc acg aaa ggc cca aag acc aac ggc ttg       624
Trp Gln Phe Gln Asn Ser Ile Thr Lys Gly Pro Lys Thr Asn Gly Leu
             160             165             170 caa gct tgg gat aca gcc aag tac tac cgc gat ctg gcc aag gtg gtc       672
Gln Ala Trp Asp Thr Ala Lys Tyr Tyr Arg Asp Leu Ala Lys Val Val
             175             180             185 gct ggc aag aag gac gcg ggc ttc aac act tcc ttc acg gac tac tgg       720
Ala Gly Lys Lys Asp Ala Gly Phe Asn Thr Ser Phe Thr Asp Tyr Trp
         190             195             200 ggt cgc gca ctc tcc tac cag ctg att aac gcg acc gac gga ggc cca       768
Gly Arg Ala Leu Ser Tyr Gln Leu Ile Asn Ala Thr Asp Gly Gly Pro
205             210             215                         220 ggc tac acc tgg tca tcg atc gct tta acc cag ggc ttc aag aac gga       816
Gly Tyr Thr Trp Ser Ser Ile Ala Leu Thr Gln Gly Phe Lys Asn Gly
             225             230             235 aac atg ccc atg ccg ctc ctt gtc gcc gac ggc cgc aac cca ggc gag       864
Asn Met Pro Met Pro Leu Leu Val Ala Asp Gly Arg Asn Pro Gly Glu
         240             245             250 acc cta atc ggc agc aac tcg acc gtg tat gag ttc aac ccc tgg gaa       912
Thr Leu Ile Gly Ser Asn Ser Thr Val Tyr Glu Phe Asn Pro Trp Glu
         255             260             265 ttc ggc agt ttt gat ccg tcc atc ttc ggc ttc gct ccc ctc gaa tac       960
Phe Gly Ser Phe Asp Pro Ser Ile Phe Gly Phe Ala Pro Leu Glu Tyr
     270             275             280 ctc gga tcc tac ttt gag aac ggc gaa gtc cca tcc agc cga tcc tgc      1008
Leu Gly Ser Tyr Phe Glu Asn Gly Glu Val Pro Ser Ser Arg Ser Cys
285             290             295             300
```

```
gtc cgc ggc ttc gat aac gca ggc ttc gtc atg gga acc tcc tcc agt      1056
Val Arg Gly Phe Asp Asn Ala Gly Phe Val Met Gly Thr Ser Ser Ser
            305                 310                 315 ctc ttc aac caa ttc atc ctg aag ctc aac acc acc gac atc cca tca      1104
Leu Phe Asn Gln Phe Ile Leu Lys Leu Asn Thr Thr Asp Ile Pro Ser
            320                 325                 330 acc ctc aaa acg gtc atc gcc agc atc cta gaa gaa cta ggc gac cgc      1152
Thr Leu Lys Thr Val Ile Ala Ser Ile Leu Glu Glu Leu Gly Asp Arg
            335                 340                 345 aac gac gac atc gcc atc tac tct ccc aac ccc ttc tac ggg tac cgc      1200
Asn Asp Asp Ile Ala Ile Tyr Ser Pro Asn Pro Phe Tyr Gly Tyr Arg
350                 355                 360 aac gcg aca gtt tca tac gaa aag acc ccg gac ctg aac gtc gtc gac      1248
Asn Ala Thr Val Ser Tyr Glu Lys Thr Pro Asp Leu Asn Val Val Asp
365                 370                 375                 380 ggt ggc gaa gac aaa cag aac ctc ccc ctc cat cct ctc atc caa ccc      1296
Gly Gly Glu Asp Lys Gln Asn Leu Pro Leu His Pro Leu Ile Gln Pro
            385                 390                 395 gcc cgc aac gtg gac gtc atc ttc gcc gtc gac tcc tca gcc agt acc      1344
Ala Arg Asn Val Asp Val Ile Phe Ala Val Asp Ser Ser Ala Ser Thr
            400                 405                 410 tcg gac aac tgg ccc aac gga agt cct ctc gtc gcg act tac gaa cgt      1392
Ser Asp Asn Trp Pro Asn Gly Ser Pro Leu Val Ala Thr Tyr Glu Arg
            415                 420                 425 agt ctc aac tca acc ggt atc gga aac ggc acc gcg ttc cct agc atc      1440
Ser Leu Asn Ser Thr Gly Ile Gly Asn Gly Thr Ala Phe Pro Ser Ile
            430                 435                 440 ccg gac aag agc acc ttc att aac ctg ggc ttg aac acc cgt ccg act      1488
Pro Asp Lys Ser Thr Phe Ile Asn Leu Gly Leu Asn Thr Arg Pro Thr
445                 450                 455                 460 ttc ttc ggc tgc aat agt tcc aat atc aca ggc cat gca ccc ctg gtt      1536
Phe Phe Gly Cys Asn Ser Ser Asn Ile Thr Gly His Ala Pro Leu Val
            465                 470                 475 gtc tac ctc ccc aac tac ccc tac aca acc ctc tcc aac aag tcg acc      1584
Val Tyr Leu Pro Asn Tyr Pro Tyr Thr Thr Leu Ser Asn Lys Ser Thr
            480                 485                 490 ttc cag ctc aag tac gag atc ttg gag cgt gat gag atg atc acc aat      1632
Phe Gln Leu Lys Tyr Glu Ile Leu Glu Arg Asp Glu Met Ile Thr Asn
            495                 500                 505 ggc tgg aac gtg gtt act atg ggt aat gga tca agg aag tct tac gag      1680
Gly Trp Asn Val Val Thr Met Gly Asn Gly Ser Arg Lys Ser Tyr Glu
510                 515                 520 gat tgg ccg act tgt gcg ggc tgc gct att ctg agt cgc tcg ttt gat      1728
Asp Trp Pro Thr Cys Ala Gly Cys Ala Ile Leu Ser Arg Ser Phe Asp
525                 530                 535                 540 cgg act aat acc cag gtg ccg gat atg tgc tcg cag tgt ttt gac aag      1776
Arg Thr Asn Thr Gln Val Pro Asp Met Cys Ser Gln Cys Phe Asp Lys
            545                 550                 555 tat tgc tgg gat gga acg agg aat agt acg acg ccg gcg gcg tat gag      1824
Tyr Cys Trp Asp Gly Thr Arg Asn Ser Thr Thr Pro Ala Ala Tyr Glu
            560                 565                 570 ccg aag gta ttg atg gct agt gcg ggt gtg agg ggt att tcg atg tcg      1872
Pro Lys Val Leu Met Ala Ser Ala Gly Val Arg Gly Ile Ser Met Ser
            575                 580                 585 agg ttg gtt ttg ggt ctc ttt ccg gtg gtg gtt ggg gtt tgg atg atg      1920
Arg Leu Val Leu Gly Leu Phe Pro Val Val Val Gly Val Trp Met Met
            590                 595                 600 tga                                                                   1923
```

<210> SEQ ID NO 2
<211> LENGTH: 640
<212> TYPE: PRT
<213> ORGANISM: Aspergillus niger

<400> SEQUENCE: 2

```
Met Lys Phe Asn Ala Leu Leu Thr Thr Leu Ala Ala Leu Gly Tyr Ile
    -35                 -30                 -25
Gln Gly Gly Ala Ala Val Pro Thr Thr Val Asp Leu Thr Tyr Ala Asp
-20                 -15                 -10                  -5
Ile Ser Pro Arg Ala Leu Asp Asn Ala Pro Asp Gly Tyr Thr Pro Ser
             -1  1               5                  10
Asn Val Ser Cys Pro Ala Asn Arg Pro Thr Ile Arg Ser Ala Ser Thr
         15                  20                  25
Leu Ser Ser Asn Glu Thr Ala Trp Val Asp Val Arg Arg Lys Gln Thr
     30                  35                  40
Val Ser Ala Met Lys Asp Leu Phe Gly His Ile Asn Met Ser Ser Phe
 45                  50                  55                  60
Asp Ala Ile Ser Tyr Ile Asn Ser His Ser Ser Asn Ile Thr Asn Ile
             65                  70                  75
Pro Asn Ile Gly Ile Ala Val Ser Gly Gly Gly Tyr Arg Ala Leu Thr
         80                  85                  90
Asn Gly Ala Gly Ala Leu Lys Ala Phe Asp Ser Arg Thr Glu Asn Ser
     95                 100                 105
Thr His Asn Gly Gln Leu Gly Gly Leu Leu Gln Ser Ala Thr Tyr Leu
    110                 115                 120
Ser Gly Leu Ser Gly Gly Gly Trp Leu Leu Gly Ser Ile Tyr Ile Asn
125                 130                 135                 140
Asn Phe Thr Thr Val Ser Asn Leu Gln Thr Tyr Lys Glu Gly Glu Val
                145                 150                 155
Trp Gln Phe Gln Asn Ser Ile Thr Lys Gly Pro Lys Thr Asn Gly Leu
            160                 165                 170
Gln Ala Trp Asp Thr Ala Lys Tyr Tyr Arg Asp Leu Ala Lys Val Val
        175                 180                 185
Ala Gly Lys Lys Asp Ala Gly Phe Asn Thr Ser Phe Thr Asp Tyr Trp
190                 195                 200
Gly Arg Ala Leu Ser Tyr Gln Leu Ile Asn Ala Thr Asp Gly Gly Pro
205                 210                 215                 220
Gly Tyr Thr Trp Ser Ser Ile Ala Leu Thr Gln Gly Phe Lys Asn Gly
            225                 230                 235
Asn Met Pro Met Pro Leu Leu Val Ala Asp Gly Arg Asn Pro Gly Glu
        240                 245                 250
Thr Leu Ile Gly Ser Asn Ser Thr Val Tyr Glu Phe Asn Pro Trp Glu
    255                 260                 265
Phe Gly Ser Phe Asp Pro Ser Ile Phe Gly Phe Ala Pro Leu Glu Tyr
270                 275                 280
Leu Gly Ser Tyr Phe Glu Asn Gly Glu Val Pro Ser Ser Arg Ser Cys
285                 290                 295                 300
Val Arg Gly Phe Asp Asn Ala Gly Phe Val Met Gly Thr Ser Ser Ser
            305                 310                 315
Leu Phe Asn Gln Phe Ile Leu Lys Leu Asn Thr Thr Asp Ile Pro Ser
        320                 325                 330
Thr Leu Lys Thr Val Ile Ala Ser Ile Leu Glu Glu Leu Gly Asp Arg
    335                 340                 345
```

```
Asn Asp Asp Ile Ala Ile Tyr Ser Pro Asn Pro Phe Tyr Gly Tyr Arg
    350                 355                 360

Asn Ala Thr Val Ser Tyr Glu Lys Thr Pro Asp Leu Asn Val Val Asp
365                 370                 375                 380

Gly Gly Glu Asp Lys Gln Asn Leu Pro Leu His Pro Leu Ile Gln Pro
                385                 390                 395

Ala Arg Asn Val Asp Val Ile Phe Ala Val Asp Ser Ala Ser Thr
            400                 405                 410

Ser Asp Asn Trp Pro Asn Gly Ser Pro Leu Val Ala Thr Tyr Glu Arg
        415                 420                 425

Ser Leu Asn Ser Thr Gly Ile Gly Asn Gly Thr Ala Phe Pro Ser Ile
    430                 435                 440

Pro Asp Lys Ser Thr Phe Ile Asn Leu Gly Leu Asn Thr Arg Pro Thr
445                 450                 455                 460

Phe Phe Gly Cys Asn Ser Ser Asn Ile Thr Gly His Ala Pro Leu Val
                465                 470                 475

Val Tyr Leu Pro Asn Tyr Pro Tyr Thr Thr Leu Ser Asn Lys Ser Thr
            480                 485                 490

Phe Gln Leu Lys Tyr Glu Ile Leu Glu Arg Asp Glu Met Ile Thr Asn
        495                 500                 505

Gly Trp Asn Val Val Thr Met Gly Asn Gly Ser Arg Lys Ser Tyr Glu
    510                 515                 520

Asp Trp Pro Thr Cys Ala Gly Cys Ala Ile Leu Ser Arg Ser Phe Asp
525                 530                 535                 540

Arg Thr Asn Thr Gln Val Pro Asp Met Cys Ser Gln Cys Phe Asp Lys
                545                 550                 555

Tyr Cys Trp Asp Gly Thr Arg Asn Ser Thr Pro Ala Ala Tyr Glu
            560                 565                 570

Pro Lys Val Leu Met Ala Ser Ala Gly Val Arg Gly Ile Ser Met Ser
        575                 580                 585

Arg Leu Val Leu Gly Leu Phe Pro Val Val Gly Val Trp Met Met
    590                 595                 600

<210> SEQ ID NO 3
<211> LENGTH: 1917
<212> TYPE: DNA
<213> ORGANISM: Aspergillus niger
<220> FEATURE:
<221> NAME/KEY: CDS
<222> LOCATION: (1)..(1914)
<223> OTHER INFORMATION:
<221> NAME/KEY: mat_peptide
<222> LOCATION: (115)..()
<223> OTHER INFORMATION:

<400> SEQUENCE: 3 atg aag ttg cct ctc ttt gct gct gca gca gct ggc ctc gcc aat gcc       48
Met Lys Leu Pro Leu Phe Ala Ala Ala Ala Ala Gly Leu Ala Asn Ala
        -35                 -30                 -25 gct tcc ctg cct gtc gaa agg gcc gag gct gag gtt gcg tcc gtc gcc       96
Ala Ser Leu Pro Val Glu Arg Ala Glu Ala Glu Val Ala Ser Val Ala
    -20                 -15                 -10 gcc gat tta atc gtc cgc gcc ctc ccc aat gcc ccc gat ggc tac act      144
Ala Asp Leu Ile Val Arg Ala Leu Pro Asn Ala Pro Asp Gly Tyr Thr
 -5              -1  1               5                  10 ccc tcc aat gtc acc tgt ccc tcg act cgt ccg agc att cgt gat gcc      192
Pro Ser Asn Val Thr Cys Pro Ser Thr Arg Pro Ser Ile Arg Asp Ala
                15                  20                  25
```

```
tcg ggc atc tcc acc aac gag acc gag tgg ctc aag gtc cgt cgc aat      240
Ser Gly Ile Ser Thr Asn Glu Thr Glu Trp Leu Lys Val Arg Arg Asn
            30                  35                  40 gcg acc ctc acc ccg atg aag aac ctc ctt agc cgt ctc aac ctc acc      288
Ala Thr Leu Thr Pro Met Lys Asn Leu Leu Ser Arg Leu Asn Leu Thr
        45                  50                  55 ggc ttt gat acc acc tcc tac atc aat gaa cac tcc agc aac atc tcc      336
Gly Phe Asp Thr Thr Ser Tyr Ile Asn Glu His Ser Ser Asn Ile Ser
    60                  65                  70 aac atc ccc aac att gca att gcg gct tcg ggt ggt gga tac cgt gcg      384
Asn Ile Pro Asn Ile Ala Ile Ala Ala Ser Gly Gly Gly Tyr Arg Ala
75                  80                  85                  90 ctc acc aac gga gct ggt gcg ctg aag gct ttc gac agc cgc tcc gac      432
Leu Thr Asn Gly Ala Gly Ala Leu Lys Ala Phe Asp Ser Arg Ser Asp
                95                  100                 105 aat gcc acc aac tcc ggt caa ctg ggt ggt ctg ctg cag gcg gca acc      480
Asn Ala Thr Asn Ser Gly Gln Leu Gly Gly Leu Leu Gln Ala Ala Thr
            110                 115                 120 tac gtc tct ggt ctg agt ggt ggt agc tgg ctg gtc gga tcc atg ttc      528
Tyr Val Ser Gly Leu Ser Gly Gly Ser Trp Leu Val Gly Ser Met Phe
        125                 130                 135 gtc aac aac ttc tcc tcc atc ggt gaa ttg caa gcc agc gag aag gtc      576
Val Asn Asn Phe Ser Ser Ile Gly Glu Leu Gln Ala Ser Glu Lys Val
    140                 145                 150 tgg cgc ttc gac aag tcc ctg ctc gag gga ccc aac ttc gac cac atc      624
Trp Arg Phe Asp Lys Ser Leu Leu Glu Gly Pro Asn Phe Asp His Ile
155                 160                 165                 170 cag atc gtc agc acg gtg gaa tac tgg aag gac att acc gag gaa gtc      672
Gln Ile Val Ser Thr Val Glu Tyr Trp Lys Asp Ile Thr Glu Glu Val
                175                 180                 185 gac ggc aag gct aac gct ggt ttt aac act tcc ttc acc gac tac tgg      720
Asp Gly Lys Ala Asn Ala Gly Phe Asn Thr Ser Phe Thr Asp Tyr Trp
            190                 195                 200 ggc cgt gcg ctg tcc tac cag ctg gtg aac gcc tcc gat gac aag ggt      768
Gly Arg Ala Leu Ser Tyr Gln Leu Val Asn Ala Ser Asp Asp Lys Gly
        205                 210                 215 ggt ccc gac tac acc tgg tcc tcc att gcg ctc atg gac gac ttc aag      816
Gly Pro Asp Tyr Thr Trp Ser Ser Ile Ala Leu Met Asp Asp Phe Lys
    220                 225                 230 aac ggc cag tac ccc atg cct att gtg gtc gcc gac ggc cgc aac ccc      864
Asn Gly Gln Tyr Pro Met Pro Ile Val Val Ala Asp Gly Arg Asn Pro
235                 240                 245                 250 ggc gaa atc atc gtt gag acc aat gcc acc gtt tat gaa gtg aac cct      912
Gly Glu Ile Ile Val Glu Thr Asn Ala Thr Val Tyr Glu Val Asn Pro
                255                 260                 265 tgg gaa ttc ggc tct ttc gac ccc agc gtc tac gcc ttc gct ccc ctg      960
Trp Glu Phe Gly Ser Phe Asp Pro Ser Val Tyr Ala Phe Ala Pro Leu
            270                 275                 280 cag tat ctg ggc tcc cgg ttc gag aac ggc tcc atc ccg gac aac ggc     1008
Gln Tyr Leu Gly Ser Arg Phe Glu Asn Gly Ser Ile Pro Asp Asn Gly
        285                 290                 295 acc tgc gtg agc ggc ttc gac aat gcc ggc ttt atc atg gga tca tcc     1056
Thr Cys Val Ser Gly Phe Asp Asn Ala Gly Phe Ile Met Gly Ser Ser
    300                 305                 310 tcc acc ctg ttc aac caa ttc ctc ctc caa atc aac agc acc agc atc     1104
Ser Thr Leu Phe Asn Gln Phe Leu Leu Gln Ile Asn Ser Thr Ser Ile
315                 320                 325                 330 ccc acg atc ctg aag gat gcc ttc act gac atc ctc gag gac ctc ggt     1152
Pro Thr Ile Leu Lys Asp Ala Phe Thr Asp Ile Leu Glu Asp Leu Gly
```

|  |  |  |  |  |  |  |  |  |  |  |  |  |  |  |  |
|---|---|---|---|---|---|---|---|---|---|---|---|---|---|---|---|
|  |  |  | 335 |  |  |  | 340 |  |  |  |  | 345 |  |  |  |
| gag | cgc | aac | gac | gat | atc | gcc | gtc | tac | tcc | ccc | aac | ccc | ttc | tcc | ggc |
| Glu | Arg | Asn | Asp | Asp | Ile | Ala | Val | Tyr | Ser | Pro | Asn | Pro | Phe | Ser | Gly |
|  |  |  | 350 |  |  |  | 355 |  |  |  |  | 360 |  |  |  |

1200 tac cgc gac agc agc gag gat tac gcc aca gcc aag gac ctc gac gtt    1248
Tyr Arg Asp Ser Ser Glu Asp Tyr Ala Thr Ala Lys Asp Leu Asp Val
            365                 370                 375 gtc gac ggt ggt gaa gac ggc gag aac atc cct ctg cac ccg ctg atc    1296
Val Asp Gly Gly Glu Asp Gly Glu Asn Ile Pro Leu His Pro Leu Ile
        380                 385                 390 cag ccc gag cgt gcc gtc gat gtc atc ttc gcc atc gac tcc tct gcc    1344
Gln Pro Glu Arg Ala Val Asp Val Ile Phe Ala Ile Asp Ser Ser Ala
395                 400                 405                 410 gac aca gac tac tac tgg ccc aac ggt acc tcc ctt gtc gcg acc tac    1392
Asp Thr Asp Tyr Tyr Trp Pro Asn Gly Thr Ser Leu Val Ala Thr Tyr
            415                 420                 425 gag cgc agt ctc gag ccc agc atc gcc aac ggc acc gcc ttc ccc gcc    1440
Glu Arg Ser Leu Glu Pro Ser Ile Ala Asn Gly Thr Ala Phe Pro Ala
        430                 435                 440 gtg ccg gat cag aac acc ttc gtc aac ctg ggt ctc aac tcc cgc ccg    1488
Val Pro Asp Gln Asn Thr Phe Val Asn Leu Gly Leu Asn Ser Arg Pro
    445                 450                 455 act ttc ttc ggc tgc gac ccc aag aac atc tcc ggc acc gcc ccc ctg    1536
Thr Phe Phe Gly Cys Asp Pro Lys Asn Ile Ser Gly Thr Ala Pro Leu
460                 465                 470 gtc att tat ctg cct aac agc ccc tac acc tac gac tcc aac ttc tcg    1584
Val Ile Tyr Leu Pro Asn Ser Pro Tyr Thr Tyr Asp Ser Asn Phe Ser
475                 480                 485                 490 acc ttc aag ctg acc tac agc gac gag gag cgt gat tcc gtc atc acc    1632
Thr Phe Lys Leu Thr Tyr Ser Asp Glu Glu Arg Asp Ser Val Ile Thr
            495                 500                 505 aac ggc tgg aac gtg gtc act cgc ggt aac ggt acc gtt gat gat aac    1680
Asn Gly Trp Asn Val Val Thr Arg Gly Asn Gly Thr Val Asp Asp Asn
        510                 515                 520 ttc ccg tct tgc gtg gcg tgc gct att ctc caa gcg ctc cac tac agg    1728
Phe Pro Ser Cys Val Ala Cys Ala Ile Leu Gln Ala Leu His Tyr Arg
    525                 530                 535 acg aac acc tct ctg cca gat atc tgt acc acc tgc ttt aac gat tac    1776
Thr Asn Thr Ser Leu Pro Asp Ile Cys Thr Thr Cys Phe Asn Asp Tyr
540                 545                 550 tgc tgg aac ggc acg aca aac agc act acg cct gga gct tat gaa ccc    1824
Cys Trp Asn Gly Thr Thr Asn Ser Thr Thr Pro Gly Ala Tyr Glu Pro
555                 560                 565                 570 agt gtg ctg att gct act agc ggt gcg atc aag agt gtc ttg gat tac    1872
Ser Val Leu Ile Ala Thr Ser Gly Ala Ile Lys Ser Val Leu Asp Tyr
            575                 580                 585 tcg gtg ctg gcg ctc gcc atg ggt gtt gct gcg ttt atg ctg tag        1917
Ser Val Leu Ala Leu Ala Met Gly Val Ala Ala Phe Met Leu
        590                 595                 600

<210> SEQ ID NO 4
<211> LENGTH: 638
<212> TYPE: PRT
<213> ORGANISM: Aspergillus niger

<400> SEQUENCE: 4

Met Lys Leu Pro Leu Phe Ala Ala Ala Ala Gly Leu Ala Asn Ala
            -35                 -30                 -25

Ala Ser Leu Pro Val Glu Arg Ala Glu Ala Glu Val Ala Ser Val Ala
        -20                 -15                 -10

```
Ala Asp Leu Ile Val Arg Ala Leu Pro Asn Ala Pro Asp Gly Tyr Thr
 -5              -1   1               5                      10

Pro Ser Asn Val Thr Cys Pro Ser Thr Arg Pro Ser Ile Arg Asp Ala
             15              20              25

Ser Gly Ile Ser Thr Asn Glu Thr Glu Trp Leu Lys Val Arg Arg Asn
             30              35              40

Ala Thr Leu Thr Pro Met Lys Asn Leu Leu Ser Arg Leu Asn Leu Thr
             45              50              55

Gly Phe Asp Thr Thr Ser Tyr Ile Asn Glu His Ser Ser Asn Ile Ser
         60              65              70

Asn Ile Pro Asn Ile Ala Ile Ala Ala Ser Gly Gly Tyr Arg Ala
 75              80              85                      90

Leu Thr Asn Gly Ala Gly Ala Leu Lys Ala Phe Asp Ser Arg Ser Asp
             95              100             105

Asn Ala Thr Asn Ser Gly Gln Leu Gly Gly Leu Leu Gln Ala Ala Thr
             110             115             120

Tyr Val Ser Gly Leu Ser Gly Gly Ser Trp Leu Val Gly Ser Met Phe
             125             130             135

Val Asn Asn Phe Ser Ser Ile Gly Glu Leu Gln Ala Ser Glu Lys Val
             140             145             150

Trp Arg Phe Asp Lys Ser Leu Leu Glu Gly Pro Asn Phe Asp His Ile
155             160             165                     170

Gln Ile Val Ser Thr Val Glu Tyr Trp Lys Asp Ile Thr Glu Glu Val
             175             180             185

Asp Gly Lys Ala Asn Ala Gly Phe Asn Thr Ser Phe Thr Asp Tyr Trp
             190             195             200

Gly Arg Ala Leu Ser Tyr Gln Leu Val Asn Ala Ser Asp Asp Lys Gly
             205             210             215

Gly Pro Asp Tyr Thr Trp Ser Ser Ile Ala Leu Met Asp Phe Lys
             220             225             230

Asn Gly Gln Tyr Pro Met Pro Ile Val Val Ala Asp Gly Arg Asn Pro
235             240             245             250

Gly Glu Ile Ile Val Glu Thr Asn Ala Thr Val Tyr Glu Val Asn Pro
             255             260             265

Trp Glu Phe Gly Ser Phe Asp Pro Ser Val Tyr Ala Phe Ala Pro Leu
             270             275             280

Gln Tyr Leu Gly Ser Arg Phe Glu Asn Gly Ser Ile Pro Asp Asn Gly
             285             290             295

Thr Cys Val Ser Gly Phe Asp Asn Ala Gly Phe Ile Met Gly Ser Ser
             300             305             310

Ser Thr Leu Phe Asn Gln Phe Leu Leu Gln Ile Asn Ser Thr Ser Ile
315             320             325             330

Pro Thr Ile Leu Lys Asp Ala Phe Thr Asp Ile Leu Glu Asp Leu Gly
             335             340             345

Glu Arg Asn Asp Asp Ile Ala Val Tyr Ser Pro Asn Pro Phe Ser Gly
             350             355             360

Tyr Arg Asp Ser Ser Glu Asp Tyr Ala Thr Ala Lys Asp Leu Asp Val
             365             370             375

Val Asp Gly Gly Glu Asp Gly Glu Asn Ile Pro Leu His Pro Leu Ile
             380             385             390

Gln Pro Glu Arg Ala Val Asp Val Ile Phe Ala Ile Asp Ser Ser Ala
395             400             405             410
```

```
Asp Thr Asp Tyr Tyr Trp Pro Asn Gly Thr Ser Leu Val Ala Thr Tyr
                415                 420                 425

Glu Arg Ser Leu Glu Pro Ser Ile Ala Asn Gly Thr Ala Phe Pro Ala
            430                 435                 440

Val Pro Asp Gln Asn Thr Phe Val Asn Leu Gly Leu Asn Ser Arg Pro
        445                 450                 455

Thr Phe Phe Gly Cys Asp Pro Lys Asn Ile Ser Gly Thr Ala Pro Leu
    460                 465                 470

Val Ile Tyr Leu Pro Asn Ser Pro Tyr Thr Tyr Asp Ser Asn Phe Ser
475                 480                 485                 490

Thr Phe Lys Leu Thr Tyr Ser Asp Glu Glu Arg Asp Ser Val Ile Thr
                495                 500                 505

Asn Gly Trp Asn Val Val Thr Arg Gly Asn Gly Thr Val Asp Asp Asn
            510                 515                 520

Phe Pro Ser Cys Val Ala Cys Ala Ile Leu Gln Ala Leu His Tyr Arg
        525                 530                 535

Thr Asn Thr Ser Leu Pro Asp Ile Cys Thr Thr Cys Phe Asn Asp Tyr
    540                 545                 550

Cys Trp Asn Gly Thr Thr Asn Ser Thr Thr Pro Gly Ala Tyr Glu Pro
555                 560                 565                 570

Ser Val Leu Ile Ala Thr Ser Gly Ala Ile Lys Ser Val Leu Asp Tyr
                575                 580                 585

Ser Val Leu Ala Leu Ala Met Gly Val Ala Ala Phe Met Leu
            590                 595                 600

<210> SEQ ID NO 5
<211> LENGTH: 1884
<212> TYPE: DNA
<213> ORGANISM: Aspergillus oryzae
<220> FEATURE:
<221> NAME/KEY: CDS
<222> LOCATION: (1)..(1881)
<223> OTHER INFORMATION:
<221> NAME/KEY: sig_peptide
<222> LOCATION: (1)..(45)
<223> OTHER INFORMATION:
<221> NAME/KEY: mat_peptide
<222> LOCATION: (70)..()
<223> OTHER INFORMATION:

<400> SEQUENCE: 5 atg aag gtc gcc ctg ctc acc tta gca gcg ggc ttg gcc aat gcc gcc        48
Met Lys Val Ala Leu Leu Thr Leu Ala Ala Gly Leu Ala Asn Ala Ala
        -20                 -15                 -10 tcg atc gcc gtc act cca cgg gcg ttc ccc aat gcc cct gat aaa tat       96
Ser Ile Ala Val Thr Pro Arg Ala Phe Pro Asn Ala Pro Asp Lys Tyr
    -5                 -1  1                   5 gct ccc gca aat gtt tcc tgt ccg tcg act cgt ccc agt atc cgc agt      144
Ala Pro Ala Asn Val Ser Cys Pro Ser Thr Arg Pro Ser Ile Arg Ser
10                  15                  20                  25 gcc gcc gcc ctg tcc acc agt gag aag gat tgg ttg caa gtg cgt cgg      192
Ala Ala Ala Leu Ser Thr Ser Glu Lys Asp Trp Leu Gln Val Arg Arg
                30                  35                  40 aat gag acc ctt gaa ccc atg aag gat ttg ctc ggg cgg ctc aat cta      240
Asn Glu Thr Leu Glu Pro Met Lys Asp Leu Leu Gly Arg Leu Asn Leu
            45                  50                  55 agc tcc ttt gat gcc tcg ggg tac att gac cgt cat aaa aac aat gca      288
Ser Ser Phe Asp Ala Ser Gly Tyr Ile Asp Arg His Lys Asn Asn Ala
        60                  65                  70 tcg aat att cca aac gtg gcc att gcc gtt tca ggt ggt ggt tac cgc      336
```

```
                                                            -continued

Ser Asn Ile Pro Asn Val Ala Ile Ala Val Ser Gly Gly Tyr Arg
    75                  80                  85 gct ttg acc aat ggc gcg ggt gct atc aag gca ttc gat agt cgt acc      384
Ala Leu Thr Asn Gly Ala Gly Ala Ile Lys Ala Phe Asp Ser Arg Thr
90                  95                  100                 105 tcc aac tcc aca gcc cgt gga cag ctc gga ggc ctt ctg cag tcc tct      432
Ser Asn Ser Thr Ala Arg Gly Gln Leu Gly Gly Leu Leu Gln Ser Ser
                110                 115                 120 act tat cta tcg ggc ctc agt ggt ggt gga tgg ctc gtg ggc tcc gtg      480
Thr Tyr Leu Ser Gly Leu Ser Gly Gly Gly Trp Leu Val Gly Ser Val
            125                 130                 135 tac atc aac aac ttc acc act atc ggt gac ctg cag gcc agc gac aag      528
Tyr Ile Asn Asn Phe Thr Thr Ile Gly Asp Leu Gln Ala Ser Asp Lys
        140                 145                 150 gtc tgg gac ttc aag aac tct att ctg gag ggt cct gat gtt aaa cat      576
Val Trp Asp Phe Lys Asn Ser Ile Leu Glu Gly Pro Asp Val Lys His
    155                 160                 165 ttc caa ctg atc aac act gcc gcg tac tgg aag gat ctg tac gat gcg      624
Phe Gln Leu Ile Asn Thr Ala Ala Tyr Trp Lys Asp Leu Tyr Asp Ala
170                 175                 180                 185 gtg aag gat aag aga aac gcc ggg ttc aac act tcg ttg acc gac tac      672
Val Lys Asp Lys Arg Asn Ala Gly Phe Asn Thr Ser Leu Thr Asp Tyr
                190                 195                 200 tgg ggc cgt gct ctc tcc tat cag ttc atc aac gct acc act gat gat      720
Trp Gly Arg Ala Leu Ser Tyr Gln Phe Ile Asn Ala Thr Thr Asp Asp
            205                 210                 215 ggc ggt ccc agt tat acc tgg tcg tcg att gcc ttg ggc gac gat ttc      768
Gly Gly Pro Ser Tyr Thr Trp Ser Ser Ile Ala Leu Gly Asp Asp Phe
        220                 225                 230 aag aag ggc aag atg ccc atg cct atc ctc gtc gcc gat gga cgt aac      816
Lys Lys Gly Lys Met Pro Met Pro Ile Leu Val Ala Asp Gly Arg Asn
    235                 240                 245 ccg ggc gaa ata ctt att gga agt aac tcg act gtg tat gaa ttt aac      864
Pro Gly Glu Ile Leu Ile Gly Ser Asn Ser Thr Val Tyr Glu Phe Asn
250                 255                 260                 265 cca tgg gag ttc ggc tcc ttc gac ccg tca gta tac ggc ttt gca cca      912
Pro Trp Glu Phe Gly Ser Phe Asp Pro Ser Val Tyr Gly Phe Ala Pro
                270                 275                 280 ttg gag tat ctt gga tcc aat ttc gag aac ggt gaa ctc ccc aag ggg      960
Leu Glu Tyr Leu Gly Ser Asn Phe Glu Asn Gly Glu Leu Pro Lys Gly
            285                 290                 295 gaa tcg tgc gtg cgc ggc ttt gac aat gcg ggt ttt gtc atg ggt acc     1008
Glu Ser Cys Val Arg Gly Phe Asp Asn Ala Gly Phe Val Met Gly Thr
        300                 305                 310 agc tct tcc ctg ttt aac cag ttc att ctg cgt ctg aac ggc acc gat     1056
Ser Ser Ser Leu Phe Asn Gln Phe Ile Leu Arg Leu Asn Gly Thr Asp
    315                 320                 325 atc cct aat ttc ctc aag gag gcg att gcc gac gtc ttg gaa cat ctg     1104
Ile Pro Asn Phe Leu Lys Glu Ala Ile Ala Asp Val Leu Glu His Leu
330                 335                 340                 345 ggc gaa aac gat gag gac att gca gtt tac gca ccc aac ccc ttc tac     1152
Gly Glu Asn Asp Glu Asp Ile Ala Val Tyr Ala Pro Asn Pro Phe Tyr
                350                 355                 360 aaa tat cgc aat tca acg gca gca tat tcg tca acc cca gag ctg gac     1200
Lys Tyr Arg Asn Ser Thr Ala Ala Tyr Ser Ser Thr Pro Glu Leu Asp
            365                 370                 375 gtg gtc gac gga ggt gaa gat gga cag aac gtg cct cta cac ccg ttg     1248
Val Val Asp Gly Gly Glu Asp Gly Gln Asn Val Pro Leu His Pro Leu
        380                 385                 390
```

```
atc cag ccc acc cac aac gtg gat gtg atc ttt gcc gtg gat tcg tcc    1296
Ile Gln Pro Thr His Asn Val Asp Val Ile Phe Ala Val Asp Ser Ser
    395                 400                 405 gct gat acg gac cat agc tgg ccc aac gga tcc tcc ttg atc tac acc    1344
Ala Asp Thr Asp His Ser Trp Pro Asn Gly Ser Ser Leu Ile Tyr Thr
410                 415                 420                 425 tat gaa cgt agc ttg aat act aca ggt atc gcc aac ggg acc tcc ttc    1392
Tyr Glu Arg Ser Leu Asn Thr Thr Gly Ile Ala Asn Gly Thr Ser Phe
                430                 435                 440 cct gcg gtg ccc gac gtc aac acg ttc ctc aac ctt ggc ctg aac aaa    1440
Pro Ala Val Pro Asp Val Asn Thr Phe Leu Asn Leu Gly Leu Asn Lys
445                 450                 455 cgc ccg acc ttc ttc gga tgc aat tca tcc aac acc agc acc ccg acc    1488
Arg Pro Thr Phe Phe Gly Cys Asn Ser Ser Asn Thr Ser Thr Pro Thr
    460                 465                 470 cca ttg att gtc tac ttg ccc aac gcc cct tac acc gcc gag tcc aac    1536
Pro Leu Ile Val Tyr Leu Pro Asn Ala Pro Tyr Thr Ala Glu Ser Asn
475                 480                 485 acg tca acc ttc cag ctg gcg tat aag gac caa caa cgc gat gat att    1584
Thr Ser Thr Phe Gln Leu Ala Tyr Lys Asp Gln Gln Arg Asp Asp Ile
490                 495                 500                 505 atc ttg aac ggc tac aac gtc gtc acc cag ggc aat gcc agt gcc gat    1632
Ile Leu Asn Gly Tyr Asn Val Val Thr Gln Gly Asn Ala Ser Ala Asp
                510                 515                 520 gca aac tgg ccc tcg tgc gtt ggg tgc gct att ctc cag cgg tcc acc    1680
Ala Asn Trp Pro Ser Cys Val Gly Cys Ala Ile Leu Gln Arg Ser Thr
                525                 530                 535 gaa cgt acg aac act aag ctt ccc gat atc tgc aat acc tgc ttc aag    1728
Glu Arg Thr Asn Thr Lys Leu Pro Asp Ile Cys Asn Thr Cys Phe Lys
                540                 545                 550 aat tac tgc tgg gac gga aag acc aac agc acc aca ccg gcc ccc tat    1776
Asn Tyr Cys Trp Asp Gly Lys Thr Asn Ser Thr Thr Pro Ala Pro Tyr
555                 560                 565 gaa ccg gag cta ttg atg gag gcg tcg act tcc ggg gcc tcg aag gat    1824
Glu Pro Glu Leu Leu Met Glu Ala Ser Thr Ser Gly Ala Ser Lys Asp
570                 575                 580                 585 caa ctg aac cgg aca gct gca gtc atc gcg ttc gca gtt atg ttc ttt    1872
Gln Leu Asn Arg Thr Ala Ala Val Ile Ala Phe Ala Val Met Phe Phe
                590                 595                 600 atg acg atc tag                                                     1884
Met Thr Ile <210> SEQ ID NO 6
<211> LENGTH: 627
<212> TYPE: PRT
<213> ORGANISM: Aspergillus oryzae

<400> SEQUENCE: 6

Met Lys Val Ala Leu Leu Thr Leu Ala Ala Gly Leu Ala Asn Ala Ala
            -20                 -15                 -10

Ser Ile Ala Val Thr Pro Arg Ala Phe Pro Asn Ala Pro Asp Lys Tyr
        -5              -1  1               5

Ala Pro Ala Asn Val Ser Cys Pro Ser Thr Arg Pro Ser Ile Arg Ser
10                  15                  20                  25

Ala Ala Ala Leu Ser Thr Ser Glu Lys Asp Trp Leu Gln Val Arg Arg
                30                  35                  40

Asn Glu Thr Leu Glu Pro Met Lys Asp Leu Leu Gly Arg Leu Asn Leu
            45                  50                  55

Ser Ser Phe Asp Ala Ser Gly Tyr Ile Asp Arg His Lys Asn Asn Ala
```

-continued

```
                60                  65                  70
Ser Asn Ile Pro Asn Val Ala Ile Ala Val Ser Gly Gly Gly Tyr Arg
    75                  80                  85
Ala Leu Thr Asn Gly Ala Gly Ala Ile Lys Ala Phe Asp Ser Arg Thr
90                  95                 100                 105
Ser Asn Ser Thr Ala Arg Gly Gln Leu Gly Gly Leu Gln Ser Ser
                   110                 115                 120
Thr Tyr Leu Ser Gly Leu Ser Gly Gly Trp Leu Val Gly Ser Val
                125                 130                 135
Tyr Ile Asn Asn Phe Thr Thr Ile Gly Asp Leu Gln Ala Ser Asp Lys
            140                 145                 150
Val Trp Asp Phe Lys Asn Ser Ile Leu Glu Gly Pro Asp Val Lys His
    155                 160                 165
Phe Gln Leu Ile Asn Thr Ala Ala Tyr Trp Lys Asp Leu Tyr Asp Ala
170                 175                 180                 185
Val Lys Asp Lys Arg Asn Ala Gly Phe Asn Thr Ser Leu Thr Asp Tyr
                190                 195                 200
Trp Gly Arg Ala Leu Ser Tyr Gln Phe Ile Asn Ala Thr Thr Asp Asp
                205                 210                 215
Gly Gly Pro Ser Tyr Thr Trp Ser Ser Ile Ala Leu Gly Asp Asp Phe
                220                 225                 230
Lys Lys Gly Lys Met Pro Met Pro Ile Leu Val Ala Asp Gly Arg Asn
    235                 240                 245
Pro Gly Glu Ile Leu Ile Gly Ser Asn Ser Thr Val Tyr Glu Phe Asn
250                 255                 260                 265
Pro Trp Glu Phe Gly Ser Phe Asp Pro Ser Val Tyr Gly Phe Ala Pro
                270                 275                 280
Leu Glu Tyr Leu Gly Ser Asn Phe Glu Asn Gly Glu Leu Pro Lys Gly
                285                 290                 295
Glu Ser Cys Val Arg Gly Phe Asp Asn Ala Gly Phe Val Met Gly Thr
            300                 305                 310
Ser Ser Ser Leu Phe Asn Gln Phe Ile Leu Arg Leu Asn Gly Thr Asp
        315                 320                 325
Ile Pro Asn Phe Leu Lys Glu Ala Ile Ala Asp Val Leu Glu His Leu
330                 335                 340                 345
Gly Glu Asn Asp Glu Asp Ile Ala Val Tyr Ala Pro Asn Pro Phe Tyr
                350                 355                 360
Lys Tyr Arg Asn Ser Thr Ala Ala Tyr Ser Ser Thr Pro Glu Leu Asp
                365                 370                 375
Val Val Asp Gly Gly Glu Asp Gly Gln Asn Val Pro Leu His Pro Leu
            380                 385                 390
Ile Gln Pro Thr His Asn Val Asp Val Ile Phe Ala Val Asp Ser Ser
    395                 400                 405
Ala Asp Thr Asp His Ser Trp Pro Asn Gly Ser Ser Leu Ile Tyr Thr
410                 415                 420                 425
Tyr Glu Arg Ser Leu Asn Thr Thr Gly Ile Ala Asn Gly Thr Ser Phe
                430                 435                 440
Pro Ala Val Pro Asp Val Asn Thr Phe Leu Asn Leu Gly Leu Asn Lys
                445                 450                 455
Arg Pro Thr Phe Phe Gly Cys Asn Ser Ser Asn Thr Ser Thr Pro Thr
                460                 465                 470
Pro Leu Ile Val Tyr Leu Pro Asn Ala Pro Tyr Thr Ala Glu Ser Asn
                475                 480                 485
```

```
Thr Ser Thr Phe Gln Leu Ala Tyr Lys Asp Gln Gln Arg Asp Asp Ile
490                 495                 500                 505

Ile Leu Asn Gly Tyr Asn Val Val Thr Gln Gly Asn Ala Ser Ala Asp
                510                 515                 520

Ala Asn Trp Pro Ser Cys Val Gly Cys Ala Ile Leu Gln Arg Ser Thr
            525                 530                 535

Glu Arg Thr Asn Thr Lys Leu Pro Asp Ile Cys Asn Thr Cys Phe Lys
        540                 545                 550

Asn Tyr Cys Trp Asp Gly Lys Thr Asn Ser Thr Thr Pro Ala Pro Tyr
    555                 560                 565

Glu Pro Glu Leu Leu Met Glu Ala Ser Thr Ser Gly Ala Ser Lys Asp
570                 575                 580                 585

Gln Leu Asn Arg Thr Ala Ala Val Ile Ala Phe Ala Val Met Phe Phe
                590                 595                 600

Met Thr Ile
```

<210> SEQ ID NO 7
<211> LENGTH: 2233
<212> TYPE: DNA
<213> ORGANISM: Aspergillus oryzae
<220> FEATURE:
<221> NAME/KEY: CDS
<222> LOCATION: (79)..(2001)
<223> OTHER INFORMATION:
<221> NAME/KEY: mat_peptide
<222> LOCATION: (193)..()
<223> OTHER INFORMATION:

<400> SEQUENCE: 7

```
gcaattcctt cgacattgct cgaaaaaaaa caacgtgtcg ctctcacgta gaactgtgtg         60
cgaccacttc aggtcagt atg aaa ccc aca aca gct gca att gct tta gcc        111
                    Met Lys Pro Thr Thr Ala Ala Ile Ala Leu Ala
                        -35                 -30 ggg ttg ctg tct ggc gtg aca gcg gcc cca ggc cct cat gga gaa agg        159
Gly Leu Leu Ser Gly Val Thr Ala Ala Pro Gly Pro His Gly Glu Arg
    -25                 -20                 -15 att gag agg att gat aga act gtg ttg gaa cgt gca ttg cca aat gct        207
Ile Glu Arg Ile Asp Arg Thr Val Leu Glu Arg Ala Leu Pro Asn Ala
-10                  -5                  -1   1               5 ccc gat gga tat gta ccg tcc aac gtc agt tgt cct gcg aat cgc ccg        255
Pro Asp Gly Tyr Val Pro Ser Asn Val Ser Cys Pro Ala Asn Arg Pro
                10                  15                  20 acg gtg cgt agc gca tca tcc ggg ctc tcg agc aat gag acc tcg tgg        303
Thr Val Arg Ser Ala Ser Ser Gly Leu Ser Ser Asn Glu Thr Ser Trp
            25                  30                  35 ttg aaa acc cga cgg gag aag act caa tct gcc atg aaa gat ttc ttc        351
Leu Lys Thr Arg Arg Glu Lys Thr Gln Ser Ala Met Lys Asp Phe Phe
        40                  45                  50 aac cat gtc acg att aag gac ttt gat gct gtc caa tat ctc gac aac        399
Asn His Val Thr Ile Lys Asp Phe Asp Ala Val Gln Tyr Leu Asp Asn
    55                  60                  65 cac tcg agt aac acg tcc aat ctt ccc aat att ggt att gcg gtg tct        447
His Ser Ser Asn Thr Ser Asn Leu Pro Asn Ile Gly Ile Ala Val Ser
70                  75                  80                  85 ggt gga ggt tat cgc gcc ctg atg aac ggt gcc gga gcg atc aaa gcg        495
Gly Gly Gly Tyr Arg Ala Leu Met Asn Gly Ala Gly Ala Ile Lys Ala
                90                  95                  100 ttt gat agc cga acg gag aac tcg acg gcg acg gga cag ttg ggt ggt        543
Phe Asp Ser Arg Thr Glu Asn Ser Thr Ala Thr Gly Gln Leu Gly Gly
```

-continued

| | | |
|---|---|---|
| ctg cta cag tcg gcg acg tat ctg gct ggt ctg agt ggt ggt gga tgg<br>Leu Leu Gln Ser Ala Thr Tyr Leu Ala Gly Leu Ser Gly Gly Gly Trp<br>120                    125                    130 | 591 |
| ctg gtg ggg tcg atc tat atc aac aat ttc acc acc att tca gca ctg<br>Leu Val Gly Ser Ile Tyr Ile Asn Asn Phe Thr Thr Ile Ser Ala Leu<br>135                    140                    145 | 639 |
| cag acc cat gag gat ggt gct gtc tgg cag ttt caa aac tcg att ttt<br>Gln Thr His Glu Asp Gly Ala Val Trp Gln Phe Gln Asn Ser Ile Phe<br>150                    155                    160                    165 | 687 |
| gag ggc cct gac ggc gat agc att cag att ctg gat tct gcg act tac<br>Glu Gly Pro Asp Gly Asp Ser Ile Gln Ile Leu Asp Ser Ala Thr Tyr<br>                    170                    175                    180 | 735 |
| tac aag cac gtt tac gat gca gtg caa gac aag aag gat gcg gga tac<br>Tyr Lys His Val Tyr Asp Ala Val Gln Asp Lys Lys Asp Ala Gly Tyr<br>                    185                    190                    195 | 783 |
| gaa acc tct atc act gat tat tgg ggt cgc gct ctc tct tat caa tta<br>Glu Thr Ser Ile Thr Asp Tyr Trp Gly Arg Ala Leu Ser Tyr Gln Leu<br>200                    205                    210 | 831 |
| atc aat gct acc gac ggc ggt ccg agc tat act tgg tcg tcc att gcc<br>Ile Asn Ala Thr Asp Gly Gly Pro Ser Tyr Thr Trp Ser Ser Ile Ala<br>215                    220                    225 | 879 |
| cta acc gat aca ttt aag cag gca gat atg ccg atg cct ctc ctc gtt<br>Leu Thr Asp Thr Phe Lys Gln Ala Asp Met Pro Met Pro Leu Leu Val<br>230                    235                    240                    245 | 927 |
| gcc gac ggt cgg tat ccc gat gag ctc gtg gtc agc agc aac gct act<br>Ala Asp Gly Arg Tyr Pro Asp Glu Leu Val Val Ser Ser Asn Ala Thr<br>                    250                    255                    260 | 975 |
| gtc tat gag ttt aac cct tgg gag ttt ggt act ttt gat cca aca gtc<br>Val Tyr Glu Phe Asn Pro Trp Glu Phe Gly Thr Phe Asp Pro Thr Val<br>                    265                    270                    275 | 1023 |
| tac ggg ttt gtg cct cta gaa tac gta ggc tct aaa ttc gac ggt ggt<br>Tyr Gly Phe Val Pro Leu Glu Tyr Val Gly Ser Lys Phe Asp Gly Gly<br>280                    285                    290 | 1071 |
| tct atc ccc gac aac gag acc tgt gta cgc gga ttc gac aac gcc ggt<br>Ser Ile Pro Asp Asn Glu Thr Cys Val Arg Gly Phe Asp Asn Ala Gly<br>295                    300                    305 | 1119 |
| ttt gtt atg ggt act tcg tca agt ttg ttc aac cag ttc ttc ctg cag<br>Phe Val Met Gly Thr Ser Ser Ser Leu Phe Asn Gln Phe Phe Leu Gln<br>310                    315                    320                    325 | 1167 |
| gtt aac tca act tcg ctt cct gat ttc ctg aag acg gca ttc tcg gac<br>Val Asn Ser Thr Ser Leu Pro Asp Phe Leu Lys Thr Ala Phe Ser Asp<br>                    330                    335                    340 | 1215 |
| atc ttg gca aag att ggt gaa gaa gat gag gac att gct gtc tat gca<br>Ile Leu Ala Lys Ile Gly Glu Glu Asp Glu Asp Ile Ala Val Tyr Ala<br>                    345                    350                    355 | 1263 |
| ccc aac ccg ttc tac aat tgg gcc ccc gtg agc tca cca gca gcc cat<br>Pro Asn Pro Phe Tyr Asn Trp Ala Pro Val Ser Ser Pro Ala Ala His<br>                    360                    365                    370 | 1311 |
| caa cag gaa ctc gat atg gtg gac ggt ggc gag gat ctt cag aac att<br>Gln Gln Glu Leu Asp Met Val Asp Gly Gly Glu Asp Leu Gln Asn Ile<br>375                    380                    385 | 1359 |
| cct ctg cat cct tta att cag cca gag cgt cac gta gat gtt atc ttt<br>Pro Leu His Pro Leu Ile Gln Pro Glu Arg His Val Asp Val Ile Phe<br>390                    395                    400                    405 | 1407 |
| gct gtt gac tcc tcc gcc gac acg act tat tct tgg ccc aac ggc aca<br>Ala Val Asp Ser Ser Ala Asp Thr Thr Tyr Ser Trp Pro Asn Gly Thr<br>                    410                    415                    420 | 1455 |
| gct ctc gtt gcc act tac gag cgc agc ctg aac tcc acc ggc atc gct | 1503 |

```
                                                                      -continued Ala Leu Val Ala Thr Tyr Glu Arg Ser Leu Asn Ser Thr Gly Ile Ala
            425                 430                 435 aac gga acc tca ttc ccc gcg atc cct gac cag aat acc ttt gtt aac       1551
Asn Gly Thr Ser Phe Pro Ala Ile Pro Asp Gln Asn Thr Phe Val Asn
        440                 445                 450 aat ggc ttg aat acg cgg cca acg ttc ttc gga tgt aac agt acg aac       1599
Asn Gly Leu Asn Thr Arg Pro Thr Phe Phe Gly Cys Asn Ser Thr Asn
    455                 460                 465 acc aca ggc cct acg cct ttg gtt gtc tac ctt ccg aac tat cca tac       1647
Thr Thr Gly Pro Thr Pro Leu Val Val Tyr Leu Pro Asn Tyr Pro Tyr
470                 475                 480                 485 gtg tct tac tcg aac tgg tca acc ttc cag cca agc tat gag atc tcc       1695
Val Ser Tyr Ser Asn Trp Ser Thr Phe Gln Pro Ser Tyr Glu Ile Ser
                490                 495                 500 gaa aga gac gac acc atc cgc aac gga tat gat gtg gtg acg atg ggt       1743
Glu Arg Asp Asp Thr Ile Arg Asn Gly Tyr Asp Val Val Thr Met Gly
            505                 510                 515 aac agc act cgt gat ggt aac tgg acg acc tgc gtc ggt tgt gct att       1791
Asn Ser Thr Arg Asp Gly Asn Trp Thr Thr Cys Val Gly Cys Ala Ile
        520                 525                 530 ctg agt cgg tct ttc gag cgc acg aac acc cag gtt ccg gat gcc tgc       1839
Leu Ser Arg Ser Phe Glu Arg Thr Asn Thr Gln Val Pro Asp Ala Cys
    535                 540                 545 acc cag tgc ttc cag aag tac tgc tgg gat ggc act acg aac tcc acc       1887
Thr Gln Cys Phe Gln Lys Tyr Cys Trp Asp Gly Thr Thr Asn Ser Thr
550                 555                 560                 565 aac cct gcc gac tat gag cct gtc acc ctg ttg gag gat agt gct ggt       1935
Asn Pro Ala Asp Tyr Glu Pro Val Thr Leu Leu Glu Asp Ser Ala Gly
                570                 575                 580 tcc gct ctc tcc ccg gct gtc atc acc acc atc gta gcg acc agt gct       1983
Ser Ala Leu Ser Pro Ala Val Ile Thr Thr Ile Val Ala Thr Ser Ala
            585                 590                 595 gct ctt ttc acc ttg ctg tgagactgga gcaattctgt tggatacggc              2031
Ala Leu Phe Thr Leu Leu
        600 tttctttctc ttttctcttc ccaggaacta ctttatata tattgcgata tatcccgact      2091 tttttttttg cttctcttca atttcttcct cctgtgcctt ttagcttgat tgtatttaag     2151 ttacatctcg gccttggcac ggtccttttt gaatatattt ctggattacc caaaaaaaa      2211 aaaaaaaaaa aaaaaaaaaa aa                                              2233

<210> SEQ ID NO 8
<211> LENGTH: 641
<212> TYPE: PRT
<213> ORGANISM: Aspergillus oryzae

<400> SEQUENCE: 8

Met Lys Pro Thr Thr Ala Ala Ile Ala Leu Ala Gly Leu Leu Ser Gly
            -35                 -30                 -25

Val Thr Ala Ala Pro Gly Pro His Gly Glu Arg Ile Glu Arg Ile Asp
        -20                 -15                 -10

Arg Thr Val Leu Glu Arg Ala Leu Pro Asn Ala Pro Asp Gly Tyr Val
    -5              -1  1                   5                   10

Pro Ser Asn Val Ser Cys Pro Ala Asn Arg Pro Thr Val Arg Ser Ala
                15                  20                  25

Ser Ser Gly Leu Ser Ser Asn Glu Thr Ser Trp Leu Lys Thr Arg Arg
            30                  35                  40

Glu Lys Thr Gln Ser Ala Met Lys Asp Phe Phe Asn His Val Thr Ile
```

-continued

```
                45                  50                  55
Lys Asp Phe Asp Ala Val Gln Tyr Leu Asp Asn His Ser Ser Asn Thr
 60                  65                  70

Ser Asn Leu Pro Asn Ile Gly Ile Ala Val Ser Gly Gly Gly Tyr Arg
 75                  80                  85                  90

Ala Leu Met Asn Gly Ala Gly Ala Ile Lys Ala Phe Asp Ser Arg Thr
                 95                 100                 105

Glu Asn Ser Thr Ala Thr Gly Gln Leu Gly Gly Leu Leu Gln Ser Ala
                110                 115                 120

Thr Tyr Leu Ala Gly Leu Ser Gly Gly Trp Leu Val Gly Ser Ile
                125                 130                 135

Tyr Ile Asn Asn Phe Thr Thr Ile Ser Ala Leu Gln Thr His Glu Asp
                140                 145                 150

Gly Ala Val Trp Gln Phe Gln Asn Ser Ile Phe Glu Gly Pro Asp Gly
155                 160                 165                 170

Asp Ser Ile Gln Ile Leu Asp Ser Ala Thr Tyr Tyr Lys His Val Tyr
                175                 180                 185

Asp Ala Val Gln Asp Lys Lys Asp Ala Gly Tyr Glu Thr Ser Ile Thr
                190                 195                 200

Asp Tyr Trp Gly Arg Ala Leu Ser Tyr Gln Leu Ile Asn Ala Thr Asp
                205                 210                 215

Gly Gly Pro Ser Tyr Thr Trp Ser Ser Ile Ala Leu Thr Asp Thr Phe
                220                 225                 230

Lys Gln Ala Asp Met Pro Met Pro Leu Leu Val Ala Asp Gly Arg Tyr
235                 240                 245                 250

Pro Asp Glu Leu Val Val Ser Ser Asn Ala Thr Val Tyr Glu Phe Asn
                255                 260                 265

Pro Trp Glu Phe Gly Thr Phe Asp Pro Thr Val Tyr Gly Phe Val Pro
                270                 275                 280

Leu Glu Tyr Val Gly Ser Lys Phe Asp Gly Gly Ser Ile Pro Asp Asn
                285                 290                 295

Glu Thr Cys Val Arg Gly Phe Asp Asn Ala Gly Phe Val Met Gly Thr
                300                 305                 310

Ser Ser Ser Leu Phe Asn Gln Phe Phe Leu Gln Val Asn Ser Thr Ser
315                 320                 325                 330

Leu Pro Asp Phe Leu Lys Thr Ala Phe Ser Asp Ile Leu Ala Lys Ile
                335                 340                 345

Gly Glu Glu Asp Glu Asp Ile Ala Val Tyr Ala Pro Asn Pro Phe Tyr
                350                 355                 360

Asn Trp Ala Pro Val Ser Ser Pro Ala Ala His Gln Gln Glu Leu Asp
                365                 370                 375

Met Val Asp Gly Gly Glu Asp Leu Gln Asn Ile Pro Leu His Pro Leu
                380                 385                 390

Ile Gln Pro Glu Arg His Val Asp Val Ile Phe Ala Val Asp Ser Ser
395                 400                 405                 410

Ala Asp Thr Thr Tyr Ser Trp Pro Asn Gly Thr Ala Leu Val Ala Thr
                415                 420                 425

Tyr Glu Arg Ser Leu Asn Ser Thr Gly Ile Ala Asn Gly Thr Ser Phe
                430                 435                 440

Pro Ala Ile Pro Asp Gln Asn Thr Phe Val Asn Asn Gly Leu Asn Thr
                445                 450                 455

Arg Pro Thr Phe Phe Gly Cys Asn Ser Thr Asn Thr Thr Gly Pro Thr
460                 465                 470
```

```
Pro Leu Val Val Tyr Leu Pro Asn Tyr Pro Tyr Val Ser Tyr Ser Asn
475                 480                 485                 490

Trp Ser Thr Phe Gln Pro Ser Tyr Glu Ile Ser Glu Arg Asp Asp Thr
            495                 500                 505

Ile Arg Asn Gly Tyr Asp Val Val Thr Met Gly Asn Ser Thr Arg Asp
            510                 515                 520

Gly Asn Trp Thr Thr Cys Val Gly Cys Ala Ile Leu Ser Arg Ser Phe
        525                 530                 535

Glu Arg Thr Asn Thr Gln Val Pro Asp Ala Cys Thr Gln Cys Phe Gln
    540                 545                 550

Lys Tyr Cys Trp Asp Gly Thr Thr Asn Ser Thr Asn Pro Ala Asp Tyr
555                 560                 565                 570

Glu Pro Val Thr Leu Leu Glu Asp Ser Ala Gly Ser Ala Leu Ser Pro
                575                 580                 585

Ala Val Ile Thr Thr Ile Val Ala Thr Ser Ala Ala Leu Phe Thr Leu
            590                 595                 600

Leu
```

<210> SEQ ID NO 9
<211> LENGTH: 30
<212> TYPE: DNA
<213> ORGANISM: Artificial Sequence
<220> FEATURE:
<223> OTHER INFORMATION: Primer
<221> NAME/KEY: misc_feature
<222> LOCATION: (9)..(9)
<223> OTHER INFORMATION: n denotes any nucleotide
<221> NAME/KEY: misc_feature
<223> OTHER INFORMATION: HU175

<400> SEQUENCE: 9
tggggccgng cactgtctta ccaactgatc                    30

<210> SEQ ID NO 10
<211> LENGTH: 29
<212> TYPE: DNA
<213> ORGANISM: Artificial Sequence
<220> FEATURE:
<223> OTHER INFORMATION: Primer
<221> NAME/KEY: misc_feature
<223> OTHER INFORMATION: HU176

<400> SEQUENCE: 10
ccgttccagc agtacctgtc aaaacacgt                     29

<210> SEQ ID NO 11
<211> LENGTH: 30
<212> TYPE: DNA
<213> ORGANISM: Artificial Sequence
<220> FEATURE:
<223> OTHER INFORMATION: Primer
<221> NAME/KEY: misc_feature
<223> OTHER INFORMATION: HU188

<400> SEQUENCE: 11
tttgatatca gacatgaagt tacctgcact                    30

<210> SEQ ID NO 12
<211> LENGTH: 30
<212> TYPE: DNA
<213> ORGANISM: Artificial Sequence
<220> FEATURE:
<223> OTHER INFORMATION: Primer

```
<221> NAME/KEY: misc_feature
<223> OTHER INFORMATION: HU189

<400> SEQUENCE: 12
tttctcgagt cacatcatcc aaaccccaac                                    30

<210> SEQ ID NO 13
<211> LENGTH: 26
<212> TYPE: DNA
<213> ORGANISM: Artificial Sequence
<220> FEATURE:
<223> OTHER INFORMATION: Primer
<221> NAME/KEY: misc_feature
<222> LOCATION: (3)..(3)
<223> OTHER INFORMATION: n in position 3 denotes any nucleotide
<221> NAME/KEY: misc_feature
<222> LOCATION: (6)..(6)
<223> OTHER INFORMATION: n in position 6  denotes any nucleotide
<221> NAME/KEY: misc_feature
<222> LOCATION: (9)..(9)
<223> OTHER INFORMATION: n in position 9  denotes any nucleotide
<221> NAME/KEY: misc_feature
<222> LOCATION: (15)..(15)
<223> OTHER INFORMATION: n in position 15  denotes any nucleotide
<221> NAME/KEY: misc_feature
<222> LOCATION: (18)..(18)
<223> OTHER INFORMATION: n in position 18 denotes any nucleotide
<221> NAME/KEY: misc_feature
<222> LOCATION: (24)..(24)
<223> OTHER INFORMATION: n in position 24 denotes any nucleotide
<221> NAME/KEY: misc_feature
<223> OTHER INFORMATION: HU212

<400> SEQUENCE: 13
gcnytnccna aygcnccnga yggnta                                        26

<210> SEQ ID NO 14
<211> LENGTH: 21
<212> TYPE: DNA
<213> ORGANISM: Artificial Sequence
<220> FEATURE:
<223> OTHER INFORMATION: Primer
<221> NAME/KEY: misc_feature
<222> LOCATION: (16)..(16)
<223> OTHER INFORMATION: n denotes in position 16 denotes any nucleotide
<221> NAME/KEY: misc_feature
<222> LOCATION: (19)..(19)
<223> OTHER INFORMATION: n denotes in position 19 denotes any nucleotide
<221> NAME/KEY: misc_feature
<223> OTHER INFORMATION: HU213

<400> SEQUENCE: 14
rtcyttccar taytcnacng t                                             21

<210> SEQ ID NO 15
<211> LENGTH: 33
<212> TYPE: DNA
<213> ORGANISM: Artificial Sequence
<220> FEATURE:
<223> OTHER INFORMATION: Primer
<221> NAME/KEY: misc_feature
<223> OTHER INFORMATION: HU225

<400> SEQUENCE: 15
tttagatcta gtcatgaagt tgcctctctt tgc                                33

<210> SEQ ID NO 16
<211> LENGTH: 30
<212> TYPE: DNA
<213> ORGANISM: Artificial Sequence
<220> FEATURE:
```

```
<223> OTHER INFORMATION: Primer
<221> NAME/KEY: misc_feature
<223> OTHER INFORMATION: HU226

<400> SEQUENCE: 16
gtttaaacta cagcataaac gcagcaacac                                   30

<210> SEQ ID NO 17
<211> LENGTH: 24
<212> TYPE: DNA
<213> ORGANISM: Artificial Sequence
<220> FEATURE:
<223> OTHER INFORMATION: Primer
<221> NAME/KEY: misc_feature
<223> OTHER INFORMATION: HU219

<400> SEQUENCE: 17
ctcgagggac ccaacttcga ccac                                         24

<210> SEQ ID NO 18
<211> LENGTH: 30
<212> TYPE: DNA
<213> ORGANISM: Artificial Sequence
<220> FEATURE:
<223> OTHER INFORMATION: Primer
<221> NAME/KEY: misc_feature
<223> OTHER INFORMATION: HU244

<400> SEQUENCE: 18
gtttaaacta cacactgggt tcataagctc                                   30

<210> SEQ ID NO 19
<211> LENGTH: 22
<212> TYPE: PRT
<213> ORGANISM: Aspergillus niger

<400> SEQUENCE: 19

Ile Val Ser Thr Val Glu Tyr Trp Lys Asp Ile Thr Glu Val Thr
1               5                   10                  15

Gly Lys Lys Asn Ala Ala
            20
```

LYSOPHOSPHOLIPASE

CROSS-REFERENCE TO RELATED APPLICATIONS

This application claims priority of Provisional application 60/160,572 filed Oct. 20, 1999 and of Danish application PA 1999 01473 filed Oct. 14, 1999, the contents of which are fully incorporated herein by reference.

FIELD OF THE INVENTION

The present invention relates to lysophospholipases (LPL), methods of using and producing them, as well as nucleic acid sequences encoding them.

BACKGROUND OF THE INVENTION

Lysophospholipases (EC 3.1.1.5) are enzymes that can hydrolyze 2-lysophospholids to release fatty acid. They are known to be useful, e.g., for improving the filterability of an aqueous solution containing a starch hydrolysate, particularly a wheat starch hydrolysate (EP 219,269).

N. Masuda et al., Eur. J. Biochem., 202, 783–787 (1991) describe an LPL from *Penicillium notatum* as a glycoprotein having a molecular mass of 95 kDa and a published amino acid sequence of 603 amino acid residues. WO 98/31790 and EP 808,903 describe LPL from *Aspergillus foetidus* and *Aspergillus niger*, each having a molecular mass of 36 kDa and an amino acid sequence of 270 amino acids.

JP-A 10-155493 describes a phospholipase A1 from *Aspergillus oryzae*. The mature protein has 269 amino acids.

SUMMARY OF THE INVENTION

The inventors have isolated lysophospholipases from Aspergillus (*A. niger* and *A. oryzae*) having molecular masses of about 68 kDa and amino acid sequences of 600–604 amino acid residues. The novel lysophospholipases have only a limited homology to known amino acid sequences. The inventors also isolated genes encoding the novel enzymes and cloned them into *E. coli* strains.

Accordingly, the invention provides a lysophospholipase which may be a polypeptide having an amino acid sequence as the mature peptide shown in one of the following or which can be obtained therefrom by substitution, deletion, and/or insertion of one or more amino acids, particularly by deletion of 25–35 amino acids at the C-terminal:

SEQ ID NO: 2 (hereinafter denoted *A. niger* LLPL-1),
SEQ ID NO: 4 (hereinafter denoted *A. niger* LLPL-2),
SEQ ID NO: 6 (hereinafter denoted *A. oryzae* LLPL-1), or
SEQ ID NO: 8 (hereinafter denoted *A. oryzae* LLPL-2).

Further, the lysophospholipase of the invention may be a polypeptide encoded by the lysophospholipase encoding part of the DNA sequence cloned into a plasmid present in *Echerichia coli* deposit number DSM 13003, DSM 13004, DSM 13082 or DSM 13083.

The lysophospholipase may also be an analogue of the polypeptide defined above which:

i) has at least 70% homology with said polypeptide,
ii) is immunologically reactive with an antibody raised against said polypeptide in purified form,
iii) is an allelic variant of said polypeptide.

Finally, the phospholipase of the invention may be a polypeptide which is encoded by a nucleic acid sequence which hybridizes under high stringency conditions with one of the following sequences or its complementary strand or a subsequence thereof of at least 100 nucleotides:

nucleotides 109–1920 of SEQ ID NO: 1 (encoding *A. niger* LLPL-1),
nucleotides 115–1914 of SEQ ID NO: 3 (encoding *A. niger* LLPL-2),
nucleotides 70–1881 of SEQ ID NO: 5 (encoding *A. oryzae* LLPL-1), or
nucleotides 193–2001 of SEQ ID NO: 7 (encoding *A. oryzae* LLPL-2).

The nucleic acid sequence of the invention may comprise a nucleic acid sequence which encodes any of the lysophospholipases described above, or it may encode a lysophospholipase and comprise:

a) the lysophospholipase encoding part of the DNA sequence cloned into a plasmid present in *Echerichia coli* DSM 13003, DSM 13004, DSM 13082 or DSM 13083 (encoding *A. niger* LLPL-1, *A. niger* LLPL-2, *A. oryzae* LLPL-1 and *A. oryzae* LLPL-2, respectively),
b) the DNA sequence shown in SEQ ID NO: 1, 3, 5 or 7 (encoding *A. niger* LLPL-1, *A. niger* LLPL-2, *A. oryzae* LLPL-1 and *A. oryzae* LLPL-2, respectively), or
c) an analogue of the DNA sequence defined in a) or b) which
i) has at least 70% homology with said DNA sequence, or
ii) hybridizes at high stringency with said DNA sequence, its complementary strand or a subsequence thereof.

Other aspects of the invention provide a recombinant expression vector comprising the DNA sequence, and a cell transformed with the DNA sequence or the recombinant expression vector.

A comparison with full-length prior-art sequences shows that the mature amino acid sequences of the invention have 60–69% homology with LPL from *Penicillium notatum* (described above), and the corresponding DNA sequences of the invention show 63–68% homology with that of *P. notatum* LPL.

A comparison with published partial sequences shows that an expressed sequence tag (EST) from *Aspergillus nidulans* (GenBank AA965865) of 155 amino acid residues can be aligned with the mature *A. oryzae* LLPL-2 of the invention (604 amino acids) with a homology of 79%.

DETAILED DESCRIPTION OF THE INVENTION

Genomic DNA Source

Lysophospholipases of the invention may be derived from strains of Aspergillus, particularly strains of *A. niger* and *A. oryzae*, using probes designed on the basis of the DNA sequences in this specification.

Strains of *Echerichia coli* containing genes encoding lysophospholipase were deposited by the inventors under the terms of the Budapest Treaty with the DSMZ—Deutsche Sammlung von Microorganismen und Zellkulturen GmbH, Mascheroder Weg 1b, D-38124 Braunschweig DE as follows:

| Source organism | Designation of lysophospholipase | Accession number | Date deposited |
| --- | --- | --- | --- |
| *A. niger* | LLPL-1 | DSM 13003 | Aug. 18, 1999 |
| *A. niger* | LLPL-2 | DSM 13004 | Aug. 18, 1999 |

-continued

| Source organism | Designation of lysophospholipase | Accession number | Date deposited |
|---|---|---|---|
| A. oryzae | LLPL-1 | DSM 13082 | Oct. 8, 1999 |
| A. oryzae | LLPL-2 | DSM 13083 | Oct. 8, 1999 |

C-terminal Deletion

The lysophospholipase may be derived from the mature peptide shown in SEQ ID NOS: 2, 4, 6 or 8 by deletion at the C-terminal to remove the ω site residue while preserving the lysophospholipase activity. The ω site residue is described in Yoda et al. Biosci. Biotechnol. Biochem. 64, 142–148, 2000, e.g. S577 of SEQ ID NO: 4. Thus, the C-terminal deletion may particularly consist of 25–35 amino acid residues.

A lysophospholipase with a C-terminal deletion may particularly be produced by expression in a strain of A. oryzae.

Properties of Lysophospholipase

The lysophospholipase of the invention is able to hydrolyze fatty acyl groups in lysophospholipid such as lysolecithin (Enzyme Nomenclature EC 3.1.1.5). It may also be able to release fatty acids from intact phospholipid (e.g. lecithin).

Recombinant Expression Vector

The expression vector of the invention typically includes control sequences encoding a promoter, operator, ribosome binding site, translation initiation signal, and, optionally, a selectable marker, a transcription terminator, a repressor gene or various activator genes. The vector may be an autonomously replicating vector, or it may be integrated into the host cell genome.

Production by Cultivation of Transformant

The lysophospholipase of the invention may be produced by transforming a suitable host cell with a DNA sequence encoding the phospholipase, cultivating the transformed organism under conditions permitting the production of the enzyme, and recovering the enzyme from the culture.

The host organism is preferably a eukaryotic cell, in particular a fungal cell, such as a yeast cell or a filamentous fungal cell, such as a strain of Aspergillus, Fusarium, Trichoderma or Saccharomyces, particularly A. niger, A. oryzae, F. graminearum, F. sambucinum, F. cerealis or S. cerevisiae, e.g. a glucoamylase-producing strain of A. niger such as those described in U.S. Pat. No. 3,677,902, or a mutant thereof. The production of the lysophospholipase in such host organisms may be done by the general methods described in EP 238,023 (Novo Nordisk), WO 96/00787 (Novo Nordisk) or EP 244,234 (Alko).

Hybridization

The hybridization is used to indicate that a given DNA sequence is analogous to a nucleotide probe corresponding to a DNA sequence of the invention. The hybridization conditions are described in detail below.

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 μg/ml of denatured sonicated salmon sperm DNA (Sambrook et al. 1989), followed by hybridization in the same solution containing a random-primed (Feinberg, A. P. and Vogelstein, B. (1983) Anal. Biochem. 132:6–13), $^{32}$P-dCTP-labeled (specific activity>1×10$^9$ cpm/μg) probe for 12 hours at approx. 45° C. The filter is then washed two times for 30 minutes in 2×SSC, 0.5% SDS at a temperature of at least 55° C., more preferably at least 60° C., more preferably at least 65° C., even more preferably at least 70° C., especially at least 75° C.

Molecules to which the oligonucleotide probe hybridizes under these conditions are detected using a x-ray film.

Alignment and Homology

The lysophospholipase and the nucleotide sequence of the invention preferably have homologies to the disclosed sequences of at least 80%, particularly at least 90% or at least 95%, e.g. at least 98%.

For purposes of the present invention, alignments of sequences and calculation of homology scores were done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment is from the FASTA package version v20u6 (W. R. Pearson and D. J. Lipman (1988), "Improved Tools for Biological Sequence Analysis", PNAS 85:2444–2448, and W. R. Pearson (1990) "Rapid and Sensitive Sequence Comparison with FASTP and FASTA", Methods in Enzymology, 183:63–98). Multiple alignments of protein sequences were done using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680). Multiple alignment of DNA sequences are done using the protein alignment as a template, replacing the amino acids with the corresponding codon from the DNA sequence.

Lysophospholipase Activity (LLU)

Lysophospholipase activity is measured using egg yolk L-α-lysolecithin as the substrate with a NEFA C assay kit. 20 μl of sample is mixed with 100 μl of 20 mM sodium acetate buffer (pH 4.5) and 100 μl of 1% L-α-lysolecithin solution, and incubated at 55° C. for 20 min. After 20 min, the reaction mixture is transferred to the tube containing 30 μl of Solution A in NEFA kit preheated at 37° C. After 10 min incubation at 37° C., 600 μl of Solution B in NEFA kit is added to the reaction mixture and incubated at 37° C. for 10 min. Activity is measured at 555 nm on a spectrophotometer. One unit of lysophospholipase activity (1 LLU) is defined as the amount of enzyme that can increase the A550 of 0.01 per minute at 55° C.

Use of Lysophospholipase

The lysophospholipase of the invention can be used in any application where it is desired to hydrolyze the fatty acyl group(s) of a phospholipid or lysophospholipid, such as lecithin or lyso-lecithin.

As an example, the lysophospholipase of the invention can be used in the preparation of dough, bread and cakes, e.g. to improve the elasticity of the bread or cake. Thus, the lysophospholipase can be used in a process for making bread, comprising adding the lysophospholipase to the ingredients of a dough, kneading the dough and baking the dough to make the bread. This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.) or EP 426211 (Unilever).

The lysophospholipase of the invention can also be used to improve the filterability of an aqueous solution or slurry of carbohydrate origin by treating it with the lysophospholipase. This is particularly applicable to a solution or slurry containing a starch hydrolysate, especially a wheat starch hydrolysate since this tends to be difficult to filter and to give cloudy filtrates. The lysophospholipase may advantageously be used together with a beta-glucanase and/or a xylanase, e.g. as described in EP 219,269 (CPC International).

The lysophospholipase of the invention can be used in a process for reducing the content of phospholipid in an edible oil, comprising treating the oil with the lysophospholipase so as to hydrolyze a major part of the phospholipid, and separating an aqueous phase containing the hydrolyzed phospholipid from the oil. This process is applicable to the purification of any edible oil which contains phospholipid, e.g. vegetable oil such as soy bean oil, rape seed oil and sunflower oil. The process can be conducted according to principles known in the art, e.g. in analogy with U.S. Pat. No. 5,264,367 (Metaligesellschaft, Röhm); K. Dahlke & H. Buchold, INFORM, 6 (12), 1284–91 (1995); H. Buchold, Fat Sci. Technol., 95 (8), 300–304 (1993); JP-A 2-153997 (Showa Sangyo); or EP 654,527 (Metaligesellschaft, Röhm).

EXAMPLES

Materials and Methods

Methods

Unless otherwise stated, DNA manipulations and transformations were performed using standard methods of molecular biology as described in Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology", John Wiley and Sons, 1995; Harwood, C. R., and Cutting, S. M. (eds.) "Molecular Biological Methods for Bacillus". John Wiley and Sons, 1990.

Enzymes

Enzymes for DNA manipulations (e.g. restriction endonucleases, ligases etc.) are obtainable from New England Biolabs, Inc. and were used according to the manufacturer's instructions.

Plasmids/vectors pT7Blue (Invitrogen, Netherlands)

pUC19 (Genbank Accession #: X02514)

pYES 2.0 (Invitrogen, USA).

Microbial Strains

E. coli JM109 (TOYOBO, Japan)

E. coli DH12α (GIBCO BRL, Life Technologies, USA)

Aspergillus oryzae strain IFO 4177 is available from Institute for Fermentation, Osaka (IFO) Culture Collection of Microorganisms, 17–85, Juso-honmachi, 2-chome, Yodogawa-ku, Osaka 532–8686, Japan.

A. oryzae BECh-2 is described in Danish patent application PA 1999 01726. It is a mutant of JaL228 (described in WO 98/12300) which is a mutant of IFO 4177.

Reagents

NEFA test kit (Wako, Japan)

L-α-lysolecithin (Sigma, USA).

Media and Reagents

Cove: 342.3 g/L Sucrose, 20 ml/L COVE salt solution, 10 mM Acetamide, 30 g/L noble agar.

Cove-2: 30 g/L Sucrose, 20 ml/L COVE salt solution, 10 mM, Acetamide, 30 g/L noble agar.

Cove salt solution: per liter 26 g KCl, 26 g MgSO4-7aq, 76 g KH2PO4, 50 ml Cove trace metals.

Cove trace metals: per liter 0.04 g NaB4O7-10aq, 0.4 g CuSO4-5aq, 1.2 g FeSO4-7aq, 0.7 g MnSO4-aq, 0.7 g Na2MoO2-2aq, 0.7 g ZnSO4-7aq.

AMG trace metals: per liter 14.3 g ZnSO4-7aq, 2.5 g CuSO4-5aq, 0.5 g NiCl2, 13.8 g FeSO4, 8.5 g MnSO4, 3.0 g citric acid.

YPG: 4 g/L Yeast extract, 1 g/L KH2PO4, 0.5 g/L MgSO4-7aq, 5 g/L Glucose, pH 6.0.

STC: 0.8 M Sorbitol, 25 mM Tris pH 8, 25 mM CaCl2.

STPC: 40% PEG4000 in STC buffer.

Cove top agarose: 342.3 g/L Sucrose, 20 ml/L COVE salt solution, 10 mM Acetamide, 10 g/L low melt agarose.

MS-9: per liter 30 g soybean powder, 20 g glycerol, pH 6.0.

MDU-pH5: per liter 45 g maltose-1 aq, 7 g yeast extract, 12 g KH2PO4, 1 g MgSO4-7aq, 2 g K2SO4, 0.5 ml AMG trace metal solution and 25 g 2-morpholinoethanesulfonic acid, pH 5.0.

MLC: 40 g/L Glucose, 50 g/L Soybean powder, 4 g/L Citric acid, pH 5.0.

MU-1: 260 g/L Maltdextrin, 3 g/L MgSO4-7aq, 6 g/L K2SO4, 5 g/L KH2PO4, 0.5 ml/L AMG trace metal solution, 2 g/L Urea, pH 4.5.

Example 1

Cloning and Expression of LLPL-1 Gene from A. niger

Transformation in Aspergillus Strain

Aspergillus oryzae strain BECh-2 was inoculated to 100 ml of YPG medium and incubated for 16 hrs at 32° C. at 120 rpm. Pellets were collected and washed with 0.6 M KCl, and resuspended 20 ml 0.6 M KCl containing a commercial β-glucanase product (Glucanex, product of Novo Nordisk A/S) at the concentration of 30 µl/ml. Cultures were incubated at 32° C. at 60 rpm until protoplasts formed, then washed with STC buffer twice. The protoplasts were counted with a hematometer and resuspended in an 8:2:0.1 solution of STC:STPC:DMSO to a final concentration of $2.5 \times 10e7$ protoplasts/ml. About 3 µg of DNA was added to 100 µl of protoplasts solution, mixed gently and incubated on ice for 30 min. One ml of SPTC was added and incubated 30 min at 37° C. After the addition of 10 ml of 50° C. Cove top agarose, the reaction was poured onto Cove agar plate. Transformation plates were incubated at 32° C. for 5 days.

Preparation of a llp1 probe

A strain of Aspergillus niger was used as a genomic DNA supplier.

PCR reactions on Aspergillus niger genome DNA was done with the primers HU175 (SEQ ID NO: 9) and HU176 (SEQ ID NO: 10) designed based upon the alignment several lysophospholipases from Penicillium and Neurospora sp.

Reaction components (1 ng /µl of genomic DNA, 250 mM dNTP each, primer 250 nM each, 0.1 U/µl in Taq polymerase in 1×buffer (Roche Diagnostics, Japan)) were mixed and submitted for PCR under the following conditions.

| Step | Temperature | Time |
|------|-------------|------|
| 1 | 94° C. | 2 min |
| 2 | 92° C. | 1 min |
| 3 | 55° C. | 1 min |
| 4 | 72° C. | 1 min |
| 5 | 72° C. | 10 min |
| 6 | 4° C. | forever |

Steps 2 to 4 were repeated 30 times.

Steps 2 to 4 were repeated 30 times.

The expected size, 1.0 kb fragment was gel-purified with QIA gel extraction kit (Qiagen, Germany) and ligated into a pT7Blue vector with ligation high (TOYOBO, Japan). The ligation mixture was transformed into *E. coli* JM109. The resultant plasmid mid (pHUda94) was sequenced and compared to the Penicillium lysophospholipase, showing that a clone encodes the internal part of the lysophospholipase.

Cloning of llpl-1 Gene

In order to clone the missing part of the lysophospholipase gene, a genomic restriction map was constructed by using the PCR fragment as probes to a Southern blot of *Aspergillus niger* DNA digested with seven restriction enzymes, separately and probed with 1.0 kb fragment encoding partial lysophospholipase from pHUda94.

A hybridized 4–6 kb Sphl fragment was selected for a llpl-1 gene subclone.

For construction of a partial genomic library of *Aspergillus niger*, the genomic DNA was digested with Sphl and run on a 0.7% agarose gel. DNA with a size between 4 to 6 kb was purified and cloned into pUC19 pretreated Sphl and BAP (Bacterial alkaline phosphatase). The sphl sub-library was made by transforming the ligated clones into *E. coli* DH12α cells. Colonies were grown on Hybond-N+ membranes (Amersham Pharmacia Biotech, Japan) and hybridized to DIG-labelled (Non-radio isotope) 1.0 kb fragment from pHUda94.

Positive colonies were picked up and their inserts were checked by PCR. Plamids from selected colonies were prepared and sequenced revealing 5 kb Sphl fragment were containing whole llpl-1 gene.

Expression of llpl-1 Gene in *Aspergillus oryzae*

The coding region of the LLPL-1 gene was amplified from genomic DNA of an *Aspergillus niger* strain by PCR with the primers HU188 (SEQ ID NO: 11) and HU189 (SEQ ID NO: 12) which included a EcoRV and a XhoI restriction enzyme site, respectively.

Reaction components (1 ng/µl of genomic DNA, 250 mM dNTP each, primer 250 nM each, 0.1 U/µl in Taq polymerase in 1×buffer (Roche Diagnostics, Japan)) were mixed and submitted for PCR under the following conditions.

| Step | Temperature | time |
|---|---|---|
| 1 | 94° C. | 2 min |
| 2 | 92° C. | 1 min |
| 3 | 55° C. | 1 min |
| 4 | 72° C. | 2 min |
| 5 | 72° C. | 10 min |
| 6 | 4° C. | forever |

Steps 2 to 4 were repeated 30 times.

The 2 kb fragment was gel-purified with QIA gel extraction kit and ligated into a pT7Blue vector with Ligation high. The ligation mixture was transformed into *E. Coli* JM109. The resultant plasmid (pLLPL1) was sequenced. The pLLPL1 was confirmed that no changes had happen in the LLPL-1 sequences.

The pLLPL1 was digested with EcoRV and XhoI and ligated into the NurI and XhoI sites in an Aspergillus expression cassette (pCaHj483) which has *Aspergiler niger* neutral amylase promoter, *Aspergillus nidulans* TPI leader sequences, *Aspergillus niger* glucoamylase terminator and *Aspergillus nidulans* amdS gene as a marker. The resultant plasmid was named pHUda103.

The LLPL-1 expression plasmid, pHUda103, was digested with NotI and about 6.1 kb DNA fragment containing *Aspergillus niger* neutral amylase promoter, LLPL-1 coding region, *Aspergillus niger* glucoamylase terminator and *Aspergillus nidulans* amdS gene was gel-purified with QIA gel extraction kit.

The 6.1 kb DNA fragment was transformed into *Aspergillus oryzae* BECh-2. The selected transformants were inoculated in 100 ml of MS-9 media and cultivated at 30° C. for 1 day. 3 ml of grown cell in MS-9 medium was inoculated to 100 ml of MDU-pH5 medium and cultivated at 30° C. for 3 days. The supernatant was obtained by centrifugation. The cell was opened by mixed with the equal volume of reaction buffer(50 mM KPB-pH 6.0) and glass-beads for 5 min on ice and debris was removed by centrifugation.

The lysophospholipase productivity of selected transformants was determined as the rate of hydrolysis of L-α-lysolecithin at pH 4.5 and 55° C. measured in units per ml relative to the activity of the host strain, BECh-2 which is normalized to 1.0. The results shown in the table below clearly demonstrate the absence of increased lysophospholipase activity in supernatants and the presence of increased lysophospholipase activity in cell free extracts.

| Strain | Yield. (supernatant) Relative activity | Yield (Cell fraction) Relative activity |
|---|---|---|
| BECh-2 | 1.0 | 1.0 |
| LP3 | 1.0 | 4.5 |
|  | 1.0 | 4.0 |
| LP8 | 1.0 | 6.5 |
|  | 1.0 | 5.5 |

Example 2

Cloning and Expression of LLPL-2 Gene from *A. niger*

Preparation of a llp2 Probe

The same strain of *Aspergillus niger* as in Example 1 was used as a genomic DNA supplier.

PCR reactions on *Aspergillus niger* genomic DNA was done with the primers HU212 (SEQ ID NO: 13) and HU213 (SEQ ID NO: 14) designed based upon amino acid sequences from purified lysophospholipase from AMG 400L (described in Example 4).

Reaction components (1 ng/µl of genomic DNA, 250 mM dNTP each, primer 250 nM each, 0.1 U/µl in Taq polymerase in 1×buffer (Roche Diagnostics, Japan)) were mixed and submitted for PCR under the following conditions.

| Step | Temperature | time |
|---|---|---|
| 1 | 94° C. | 2 min |
| 2 | 92° C. | 1 min |
| 3 | 50° C. | 1 min |
| 4 | 72° C. | 1 min |
| 5 | 72° C. | 10 min |
| 6 | 4° C. | forever |

Steps 2 to 4 were repeated 30 times.

The expected size, 0.6 kb fragment was gel-purified with QIA gel extraction kit (Qiagen, Germany) and ligated into a pT7Blue vector with ligation high (TOYOBO, Japan). The ligation mixture was transformed into *E. coli* JM109. The resultant plasmid (pHUda114) was sequenced and compared to the Penicillium lysophospholipase, showing that a clone encodes the internal part of the lysophospholipase.

Cloning of of llpl-2 Gene

In order to clone the missing part of the lysophospholipase gene, a genomic restriction map was constructed by using the PCR fragment as probes to a Southern blot of *Aspergillus niger* DNA digested with seven restriction enzymes, separately and probed with 1.0 kb fragment encoding partial lysophospholipase from pHUda114.

A hybridized 4–6 kb XbaI fragment was selected for a llpl-2 gene subclone.

For construction of a partial genomic library of *Aspergillus niger*, the genomic DNA was digested with XbaI and run on a 0.7% agarose gel. DNA with a size between 4 to 6 kb was purified and cloned into pUC19 pretreated XbaI and BAP (Bacterial alkaline phosphatase). The XbaI sub-library was made by transforming the ligated clones into *E. coli* DH12α cells. Colonies were grown on Hybond-N+ membranes (Amersham Pharmacia Biotech, Japan) and hybridized to DIG-labelled (Non-radio isotope) 1.0 kb fragment from pHUda114.

Positive colonies were picked up and their inserts were checked by PCR. Plasmids from selected colonies were prepared and sequenced revealing 5 kb XbaI fragment were containing whole llpl-2 gene.

Expression of llpl-2 Gene in *Aspergillus oryzae*

The coding region of the LLPL-2 gene was amplified from genomic DNA of an *Aspergillus niger* strain by PCR with the primers HU225 (SEQ ID NO: 15) and HU226 (SEQ ID NO: 16) which included a BglII and a PmeI restriction enzyme site, respectively.

Reaction components (1 ng/μl of genomic DNA, 250 mM dNTP each, primer 250 nM each, 0.1 U/μl in Taq polymerase in 1×buffer (Roche Diagnostics, Japan)) were mixed and submitted for PCR under the following conditions.

| Step | Temperature | time |
|---|---|---|
| 1 | 94° C. | 2 min |
| 2 | 92° C. | 1 min |
| 3 | 55° C. | 1 min |
| 4 | 72° C. | 2 min |
| 5 | 72° C. | 10 min |
| 6 | 4° C. | forever |

Step 2 to 4 were repeated 30 times.

The 2 kb fragment was gel-purified with QIA gel extraction kit and ligated into a pT7Blue vector with Ligation high. The ligation mixture was transformed into *E. coli* JM109. The resultant plasmid (pLLPL2) was sequenced. The pLLPL2 was confirmed that no changes had happen in the LLPL-2 sequences.

The pLLPL2 was digested with BglII and PmeI and ligated into the BamHI and NurI sites in the Aspergillus expression cassette pCaHj483 which has *Aspergillus niger* neutral amylase promoter, *Aspergillus nidulans* TPI leader sequences, *Aspergillus niger* glucoamylase terminator and *Aspergillus nidulans* amdS gene as a marker. The resultant plasmid was pHUda123.

The LLPL-2 expression plasmid, pHUda123, was digested with NotI and about 6.0 kb DNA fragment containing *Aspergillus niger* neutral amylase promoter, LLPL-2 coding region, *Aspergillus niger* glucoamylase terminator and *Aspergillus nidulans* amdS gene was gel-purified with QIA gel extraction kit.

The 6.0 kb DNA fragment was transformed into *Aspergillus oryzae* BECh-2. The selected transformants were inoculated in 100 ml of MS-9 media and cultivated at 30° C. for 1 day. 3 ml of grown cell in MS-9 medium was inoculated to 100 ml of MDU-pH5 medium and cultivated cultivated at 30° C. for 4 days.

The supernatant was obtained by centrifugation. The cell was opened by mixed with the equal volume of reaction buffer (50 mM KPB-pH 6.0) and glass-beads for 5 min on ice and debris was removed by centrifugation.

The lysophospholipase productivity of selected transformants was determined as in Example 1. The results shown in the table below clearly demonstrate the absence of increased lysophospholipase activity in supernatants and the presence of increased lysophospholipase activity in cell free extracts.

| Strain | Yield. (supernatant) Relative activity | Yield (Cell fraction) Relative activity |
|---|---|---|
| BECh-2 | 1.0 | 1.0 |
| Fg-9 | 1.0 | 225 |
| Fg-15 | 1.0 | 18.0 |
| Fg-27 | 1.0 | 17.0 |
| Fg-33 | 1.0 | 14.5 |

Example 3

Cloning and Expression of LLPL Genes from *E. coli* Clones

Each of the following large molecular weight lysophospholipase (LLPL) genes is cloned from the indicated *E. coli* clone as genomic DNA supplier, and the gene is expressed in *A. oryzae* as described in Examples 1 and 2.

| *E. coli* clone | LLPL |
|---|---|
| DSM 13003 | *A. niger* LLPL-1 |
| DSM 13004 | *A. niger* LLPL-2 |
| DSM 13082 | *A. oryzae* LLPL-1 |
| DSM 13083 | *A. oryzae* LLPL-2 |

Example 4

Isolation of *A. niger* LLPL-2 from AMG 300L

Purification of LLPL-2 from AMG 300L

A commercially available glucoamylase preparation from *A. niger* (AMG 300L, product of Novo Nordisk A/S) was diluted 10-fold with Milli-Q water and subsequently added ammonium sulfate to 80% saturation. The solution was stirred 1 hour at 4° C. followed by centrifugation on an Sorvall RC-3B centrifuge, equipped with a GSA rotor head (4500 rpm for 35 min). The precipitate was discarded and the supernatant dialysed against 50 mM sodium acetate, pH 5.5. The dialysed solution was applied to a Q-Sepharose (2.6×4 cm) column in 50 mM sodium acetate, pH 5.5 at a flow rate of 300 ml h$^{-1}$. The column was washed (10× column volume) and proteins were eluted using a linear gradient of 0–0.35 M NaCl in 50 mM sodium acetate, pH 5.5 at a flow rate of 300 ml h$^{-1}$. Fractions containing activity were pooled, concentrated on an Amicon cell (10 kDa cutoff) to 2.5 ml and applied to Superdex 200 H/R (1.6×60 cm) in 0.2 mM sodium acetate, pH 5.5 by draining into the bed. Proteins were eluted isocratically at a flow rate of 30 ml h$^{-1}$. The purified enzyme showed a specific activity of 86 LLU/mg.

SDS-PAGE analysis showed three protein bands at around 40, 80, and 120 kDa. N-terminal sequencing of the first 23 amino acids revealed that the protein bands at 40 and 120 kDa had identical sequences (shown at the N-terminal of SEQ ID NO: 4), whereas the protein band at 80 kDa was shown to have the sequence shown as SEQ ID NO: 19. IEF analysis showed that LLPL-2 had a pI of around 4.2.

Enzymatic Characterisation of LLPL-2

LLPL-2 was show to have a bell-shaped pH-activity profile with optimal activity at pH 4.0. The temperature optimum was found at 50° C. The enzyme activity was completely stable at pH 4.5 after up to 120 hours incubation at pH 4.5 and 50° C. LLPL-2 is furthermore completely stable at 50° C., whereas a half-life of 84 hours was determined at 60° C. LLPL-2 was not found to be dependent upon addition of mineral salts like sodium or calcium.

Example 5

Identification and Sequencing of LLPL-1 and LLPL-2 Genes from *A. oryzae*

Cultivation of *A. oryzae*

*Aspergillus oryzae* strain IFO 4177 was grown in two 20-liter lab fermentors on a 10-liter scale at 34° C. using yeast extract and dextrose in the batch medium, and maltose syrup, urea, yeast extract, and trace metals in the feed. Fungal mycelia from the first lab fermentor were harvested by filtering through a cellulose filter (pore size 7–11 microns) after 27 hours, 68.5 hours, 118 hours, and 139 hours of growth. The growth conditions for the second fermentor were identical to the first one, except for a slower growth rate during the first 20 hours of fermentation. Fungal mycelia from the second lab fermentor were harvested as above after 68.3 hours of growth. The harvested mycelia were immediately frozen in liquid $N_2$ and stored at -80° C.

The *Aspergillus oryzae* strain IFO 4177 was also grown in four 20-liter lab fermentors on a 10-liter scale at 34° C. using sucrose in the batch medium, and maltose syrup, ammonia, and yeast extract in the feed. The first of the four fermentations was carried out at pH 4.0. The second of the four fermentations was carried out at pH 7.0 with a constant low agitation rate (550 rpm) to achieve the rapid development of reductive metabolism. The third of the four fermentations was carried out at pH 7.0 under phosphate limited growth by lowering the amount of phosphate and yeast extract added to the batch medium. The fourth of the four fermentations was carried out at pH 7.0 and 39° C. After 75 hours of fermentation the temperature was lowered to 34° C. At 98 hours of fermentation the addition of carbon feed was stopped and the culture was allowed to starve for the last 30 hours of the fermentation. Fungal mycelial samples from the four lab fermentors above were then collected as described above, immediately frozen in liquid $N_2$, and stored at -80° C.

*Aspergillus oryzae* strain IFO 4177 was also grown on Whatman filters placed on Cove-N agar plates for two days. The mycelia were collected, immediately frozen in liquid $N_2$, and stored at -80° C.

*Aspergillus oryzae* strain IFO 4177 was also grown at 30° C. in 150 ml shake flasks containing RS-2 medium (Kofod et al., 1994, *Journal of Biological Chemistry* 269: 29182–29189) or a defined minimal medium. Fungal mycelia were collected after 5 days of growth in the RS-2 medium and 3 and 4 days of growth in the defined minimal medium, immediately frozen in liquid $N_2$, and stored at -80° C.

Construction of Directional cDNA Libraries from *Aspergillus oryzae*

Total RNA was prepared by extraction with guanidinium thiocyanate followed by ultracentrifugation through a 5.7 M CsCl cushion (Chirgwin et al., 1979, *Biochemistry* 18: 5294–5299) using the following modifications. The frozen mycelia were ground in liquid $N_2$ to a fine powder with a mortar and a pestle, followed by grinding in a precooled coffee mill, and immediately suspended in 5 volumes of RNA extraction buffer (4 M guanidinium thiocyanate, 0.5% sodium laurylsarcosine, 25 mM sodium citrate pH 7.0, 0.1 M β-mercaptoethanol). The mixture was stirred for 30 minutes at room temperature and centrifuged (20 minutes at 10000 rpm, Beckman) to pellet the cell debris. The supernatant was collected, carefully layered onto a 5.7 M CsCl cushion (5.7 M CsCl, 10 mM EDTA, pH 7.5, 0.1% DEPC; autoclaved prior to use) using 26.5 ml supernatant per 12.0 ml of CsCl cushion, and centrifuged to obtain the total RNA (Beckman, SW 28 rotor, 25000 rpm, room temperature, 24 hours). After centrifugation the supernatant was carefully removed and the bottom of the tube containing the RNA pellet was cut off and rinsed with 70% ethanol. The total RNA pellet was transferred to an Eppendorf tube, suspended in 500 ml of TE, pH 7.6 (if difficult, heat occasionally for 5 minutes at 65° C.), phenol extracted, and precipitated with ethanol for 12 hours at -20° C. (2.5 volumes of ethanol, 0.1 volume of 3M sodium acetate pH 5.2). The RNA was collected by centrifugation, washed in 70% ethanol, and resuspended in a minimum volume of DEPC. The RNA concentration was determined by measuring $OD_{260/280}$.

The poly(A)$^+$RNA was isolated by oligo(dT)-cellulose affinity chromatography (Aviv & Leder, 1972, *Proceedings of the National Academy of Sciences USA* 69: 1408–1412). A total of 0.2 g of oligo(dT) cellulose (Boehringer Mannheim, Indianapolis, Ind.) was preswollen in 10 ml of 1×of column loading buffer (20 mM Tris-Cl, pH 7.6, 0.5 M NaCl, 1 mM EDTA, 0.1% SDS), loaded onto a DEPC-treated, plugged plastic column (Poly Prep Chromatography Column, BioRad, Hercules, Calif.), and equilibrated with 20 ml of 1×loading buffer. The total RNA (1–2 mg) was heated at 65° C. for 8 minutes, quenched on ice for 5 minutes, and after addition of 1 volume of 2×column loading buffer to the RNA sample loaded onto the column. The eluate was collected and reloaded 2–3 times by heating the sample as above and quenching on ice prior to each loading. The oligo(dT) column was washed with 10 volumes of 1×loading buffer, then with 3 volumes of medium salt buffer (20 mM Tris-Cl, pH 7.6, 0.1 M NaCl, 1 mM EDTA, 0.1% SDS), followed by elution of the poly(A)$^+$RNA with 3 volumes of elution buffer (10 mM Tris-Cl, pH 7.6, 1 mM EDTA, 0.05% SDS) preheated to 65° C., by collecting 500 μl fractions. The $OD_{260}$ was read for each collected fraction, and the mRNA containing fractions were pooled and ethanol precipitated at -20° C. for 12 hours. The poly(A)$^+$RNA was collected by centrifugation, resuspended in DEPC-DIW and stored in 5–10 mg aliquots at -80° C.

Double-stranded cDNA was synthesized from 5 μg of *Aspergillus oryzae* IFO 4177 poly(A)$^+$RNA by the RNase H method (Gubler and Hoffman 1983, supra; Sambrook et al., 1989, supra) using a hair-pin modification. The poly(A)$^+$ RNA (5 μg in 5 μl of DEPC-treated water) was heated at 70° C. for 8 minutes in a pre-siliconized, RNase-free Eppendorf tube, quenched on ice, and combined in a final volume of 50 il with reverse transcriptase buffer (50 mM Tris-Cl pH 8.3, 75 mM KCl, 3 mM $MgCl_2$, 10 mM DTT) containing 1 mM of dATP, dGTP and dTTP, and 0.5 mM of 5-methyl-dCTP, 40 units of human placental ribonuclease inhibitor, 4.81 μg of oligo(dT)$_{18}$-NotI primer and 1000 units of SuperScript II RNase H-reverse transcriptase.

First-strand cDNA was synthesized by incubating the reaction mixture at 45° C. for 1 hour. After synthesis, the mRNA:cDNA hybrid mixture was gel filtrated through a Pharmacia MicroSpin S-400 HR spin column according to the manufacturer's instructions.

After the gel filtration, the hybrids were diluted in 250 μl of second strand buffer (20 mM Tris-Cl pH 7.4, 90 mM KCl, 4.6 mM $MgCl_2$, 10 mM $(NH_4)_2SO_4$, 0.16 mM βNAD$^+$) containing 200 iM of each dNTP, 60 units of *E. coli* DNA polymerase I (Pharmacia, Uppsala, Sweden), 5.25 units of RNase H, and 15 units of *E. coli* DNA ligase. Second strand cDNA synthesis was performed by incubating the reaction tube at 16° C. for 2 hours, and an additional 15 minutes at 25° C. The reaction was stopped by addition of EDTA to 20 mM final concentration followed by phenol and chloroform extractions.

The double-stranded cDNA was ethanol precipitated at -20° C. for 12 hours by addition of 2 volumes of 96% ethanol and 0.2 volume of 10 M ammonium acetate, recovered by centrifugation, washed in 70% ethanol, dried (SpeedVac), and resuspended in 30 ml of Mung bean nuclease buffer (30 mM sodium acetate pH 4.6, 300 mM NaCl, 1 mM $ZnSO_4$, 0.35 mM dithiothreitol, 2% glycerol) containing 25 units of Mung bean nuclease. The single-stranded hair-pin DNA was clipped by incubating the reaction at 30° C. for 30 minutes, followed by addition of 70 ml of 10 mM Tris-Cl, pH 7.5, 1 mM EDTA, phenol extraction, and ethanol precipitation with 2 volumes of 96% ethanol and 0.1 volume 3 M sodium acetate pH 5.2 on ice for 30 minutes.

The double-stranded cDNAs were recovered by centrifugation (20,000 rpm, 30 minutes), and blunt-ended with T4 DNA polymerase in 30 µl of T4 DNA poly-merase buffer (20 mM Tris-acetate, pH 7.9, 10 mM magnesium acetate, 50 mM potassium acetate, 1 mM dithiothreitol) containing 0.5 mM of each dNTP, and 5 units of T4 DNA polymerase by incubating the reaction mixture at +16° C. for 1 hour. The reaction was stopped by addition of EDTA to 20 mM final concentration, followed by phenol and chloroform extractions and ethanol precipitation for 12 h at −20° C. by adding 2 volumes of 96% ethanol and 0.1 volume of 3M sodium acetate pH 5.2.

After the fill-in reaction the cDNAs were recovered by centrifugation as above, washed in 70% ethanol, and the DNA pellet was dried in a SpeedVac. The cDNA pellet was resuspended in 25 µl of ligation buffer (30 mM Tris-Cl, pH 7.8, 10 mM $MgCl_2$, 10 mM dithiothreitol, 0.5 mM ATP) containing 2 µg EcoRI adaptors (0.2 µg/µl, Pharmacia, Uppsala, Sweden) and 20 units of T4 ligase by incubating the reaction mix at 16° C. for 12 hours. The reaction was stopped by heating at 65° C. for 20 minutes, and then placed on ice for 5 minutes. The adapted cDNA was digested with NotI by addition of 20 µl autoclaved water, 5 µl of 10×NotI restriction enzyme buffer and 50 units of NotI, followed by incubation for 3 hours at 37° C. The reaction was stopped by heating the sample at 65° C. for 15 minutes. The cDNAs were size-fractionated by agarose gel electrophoresis on a 0.8% SeaPlaque GTG low melting temperature agarose gel (FMC, Rockland, Me.) in 1×TBE (in autoclaved water) to separate unligated adaptors and small cDNAs. The gel was run for 12 hours at 15 V, and the cDNA was size-selected with a cut-off at 0.7 kb by cutting out the lower part of the agarose gel. Then a 1.5% agarose gel was poured in front of the cDNA-containing gel, and the double-stranded cDNAs were concentrated by running the gel backwards until it appeared as a compressed band on the gel. The cDNA-containing gel piece was cut out from the gel and the cDNA was extracted from the gel using the GFX gel band purification kit (Amersham, Arlington Heights, Ill.) as follows. The trimmed gel slice was weighed in a 2 ml Biopure Eppendorf tube, then 10 ml of Capture Buffer was added for each 10 mg of gel slice, the gel slice was dissolved by incubation at 60° C. for 10 minutes, until the agarose was completely solubilized, the sample at the bottom of the tube by brief centrifugation. The melted sample was transferred to the GFX spin column placed in a collection tube, incubated at 25° C. for 1 minite, and then spun at full speed in a microcentrifuge for 30 seconds. The flow-through was discarded, and the column was washed with 500 µl of wash buffer, followed by centrifugation at full speed for 30 seconds. The collection tube was discarded, and the column was placed in a 1.5 ml Eppendorf tube, followed by elution of the cDNA by addition of 50 µl of TE pH 7.5 to the center of the column, incubation at 25° C. for 1 minute, and finally by centrifugation for 1 minute at maximum speed. The eluted cDNA was stored at −20° C. until library construction.

A plasmid DNA preparation for a EcoRI-NotI insert-containing pYES2.0 cDNA clone, was purified using a QIAGEN Tip-100 according to the manufacturer's instructions (QIAGEN, Valencia, Calif. A total of 10 mg of purified plasmid DNA was digested to completion with NotI and EcoRI in a total volume of 60 il by addition of 6 ml of 10×NEBuffer for EcoRI (New England Biolabs, Beverly, Mass.), 40 units of NotI, and 20 units of EcoRI followed by incubation for 6 hours at 37° C. The reaction was stopped by heating the sample at 65° C. for 20 minutes. The digested plasmid DNA was extracted once with phenol-chloroform, then with chloroform, followed by ethanol precipitation for 12 hours at −20° C. by adding 2 volumes of 96% ethanol and 0.1 volume of 3 M sodium acetate pH 5.2. The precipitated DNA was resuspended in 25 ml of 1×TE pH 7.5, loaded on a 0.8% SeaKem agarose gel in 1×TBE, and run on the gel for 3 hours at 60 V. The digested vector was cut out from the gel, and the DNA was extracted from the gel using the GFX gel band purification kit (Amersham Pharmacia Biotech, Uppsala, Sweden) according to the manufacturer's instructions. After measuring the DNA concentration by $OD_{260/280}$, the eluted vector was stored at −20° C. until library construction.

To establish the optimal ligation conditions for the cDNA library, four test ligations were carried out in 10 il of ligation buffer (30 mM Tris-Cl pH 7.8, 10 mM $MgCl_2$, 10 mM DTT, 0.5 mM ATP) containing 7 µl of double-stranded cDNA, (corresponding to approximately 1/10 of the total volume in the cDNA sample), 2 units of T4 ligase, and 25 ng, 50 ng and 75 ng of EcoRI-NotI cleaved pYES2.0 vector, respectively (In-vitrogen). The vector background control ligation reaction contained 75 ng of EcoRI-NotI cleaved pYES.0 vector without cDNA. The ligation reactions were performed by incubation at 16° C. for 12 hours, heated at 65° C. for 20 minutes, and then 10 µl of autoclaved water was added to each tube. One il of the ligation mixtures was electroporated (200 W, 2.5 kV, 25 mF) to 40 µl electrocompetent *E. coli* DH10B cells (Life Technologies, Gaithersburg, Md). After addition of 1 ml SOC to each transformation mix, the cells were grown at 37° C. for 1 hour, 50 µl and 5 µl from each electroporation were plated on LB plates supplemented with ampicillin at 100 µg per ml and grown at 37° C. for 12 hours. Using the optimal conditions, 18 *Aspergillus oryzae* IFO 4177 cDNA libraries containing 1–2.5×10$^7$ independent colony forming units was established in *E. coli*, with a vector background of ca. 1%. The cDNA library was stored as (1) individual pools (25,000 c.f.u./pool) in 20% glycerol at −80° C.; (2) cell pellets of the same pools at −20° C.; (3) Qiagen purified plasmid DNA from individual pools at −20° C. (Qiagen Tip 100); and (4) directional, double-stranded cDNA at −20° C.

*Aspergillus oryzae* EST (Expressed Sequence Tag) Template Preparation

From each cDNA library described, transformant colonies were picked directly from the transformation plates into 96-well microtiter dishes (QIAGEN, GmbH, Hilden Germany) which contained 200 µl TB broth (Life Technologies, Frederick Md.) with 100, µg ampicillin per ml. The plates were incubated 24 hours with agitation (300 rpm) on a rotary shaker. To prevent spilling and cross-contamination, and to allow sufficient aeration, the plates were covered with a microporous tape sheet AirPore™ (QIAGEN GmbH, Hilden Germany). DNA was isolated from each well using the QIA prep 96 Turbo kit (QIAGEN GmbH, Hilden Germany).

EST Sequencing and Analysis of Nucleotide Sequence Data of the *Aspergillus oryzae* EST Library Single-pass DNA sequencing of the *Aspergillus oryzae* ESTs was done with a Perkin-Elmer Applied Biosystems Model 377 XL Automatic DNA Sequencer (Perkin-Elmer Applied Biosystems, Inc., Foster City, Calif.) using dye-terminator chemistry (Giesecke et al., 1992, *Journal of Virology Methods* 38: 47–60) and a pYES specific primer (Invitrogen, Carlsbad, Calif.). Vector sequence and low quality 3' sequence were removed with the pregap program from the Staden package (MRC, Cambridge, England). The sequences were assembled with TIGR Assembler software (Sutton et al., 1995, supra). The assembled sequences were searched with fastx3 (see Pearson and Lipman, 1988, *Proceedings of the National Academy of Science USA* 85: 2444–2448; Pearson, 1990, *Methods in Enzymology* 183: 63–98) against a customized database consisting of protein sequences from SWISSPROT, SWISSPROT-NEW, TREMBL, TREMBLNEW, REMTREMBL, PDB and GeneSeqP. The matrix used was BL50.

Nucleotide Sequence Analysis

The nucleotide sequence of the lysophospholipase cDNA clones pEST204, and pEST1648 were determined from both strands by the dideoxy chain-termination method (Sanger, F., Nicklen, S., and Coulson, A. R. (1977) Proc. Natl. Acad. Sci. U.S.A. 74, 5463–5467) using 500 ng of Qiagen-purified template (Qiagen, USA), the Taq deoxy-terminal cycle sequencing kit (Perkin-Elmer, USA), fluorescent labeled terminators and 5 pmol of either pYES 2.0 polylinker primers (Invitrogen, USA) or synthetic oligonucleotide primers. Analysis of the sequence data was performed according to Devereux et al., 1984 (Devereux, J., Haeberli, P., and Smithies, O. (1984) Nucleic Acids Res. 12, 387–395).

Example 6

Expression of LLPL-2 in *Aspergillus oryzae* and *Aspergillus niger*

Transformation in Aspergillus Strain

*Aspergillus oryzae* strain BECh-2 and an *Aspergillus niger* strain were each inoculated to 100 ml of YPG medium and incubated for 16 hrs at 32° C. at 120 rpm. Pellets were collected and washed with 0.6 M KCl, and resuspended 20 ml 0.6 M KCl containing Glucanex at the concentration of 30 µl/ml. Cultures were incubated at 32° C. at 60 rpm until protoplasts formed, then washed with STC buffer twice. The protoplasts were counted with a hematometer and resuspended in an 8:2:0.1 solution of STC:STPC:DMSO to a final concentration of 2.5×10e7 protoplasts/ml. About 3 µg of DNA was added to 100 µl of protoplasts solution, mixed gently and incubated on ice for 30 min. One ml of SPTC was added and incubated 30 min at 37° C. After the addition of 10 ml of 50° C. Cove top agarose, the reaction was poured onto Cove agar plate. Transformation plates were incubated at 32° C. for 5 days.

Expression of LLPL-2 Gene in *Aspergillus niger*

The coding region of the LLPL-2 gene was amplified from genomic DNA of an *Aspergillus niger* strain by PCR with the primers HU225 (SEQ ID NO: 15) and HU226 (SEQ ID NO: 16) which included a Bglll and a PmeI restriction enzyme site, respectively.

Reaction components (1 ng/µl of genomic DNA, 250 mM dNTP each, primer 250 nM each, 0.1 U/µl in Taq polymerase in 1×buffer (Roche Diagnostics, Japan)) were mixed and submitted for PCR under the following conditions.

| Step | Temperature | time |
|---|---|---|
| 1 | 94° C. | 2 min |
| 2 | 92° C. | 1 min |
| 3 | 55° C. | 1 min |
| 4 | 72° C. | 2 min |
| 5 | 72° C. | 10 min |
| 6 | 4° C. | forever |

Step 2 to 4 were repeated 30 times.

The 2 kb fragment was gel-purified with QIA gel extraction kit and ligated into a PT2Blue vector with Ligation high. The ligation mixture was transformed into *E. coli* JM109. The resultant plasmid (pLLPL2) was sequenced, and it was confirmed that no changes had happened in the LLPL-2 sequences.

The pLLPL2 was digested with Bglll and PmeI and ligated into the BamHI and NurI sites in the Aspergillus expression cassette pCaHj483 which has *Aspergillus niger* neutral amylase promoter, *Aspergillus nidulans* TPI leader sequences, *Aspergillus niger* glucoamylase terminator and *Aspergillus nidulans* amdS gene as a marker. The resultant plasmid was named pHUda123.

The LLPL-2 expression plasmid, pHUda123, was transformed into an *Aspergillus niger* strain. Selected transformants were inoculated in 100 ml of MLC media and activated at 30° C. for 2 days. 5 ml of grown cell in MLC medium was inoculated to 100 ml of MU-1 medium and cultivated at 30° C. for 7 days.

Supernatant was obtained by centrifugation, and the lysophospholipase activity was measured as described above. The table below shows the lysopholpase activity from of the selected transformants, relative to the activity of the host strain, MBin114 which was normalized to 1.0.

| Strain | Yield (supernatant) Relative activity |
|---|---|
| MBin114 | 1.0 |
| 123N-33 | 63 |
| 123N-38 | 150 |
| 123N-46 | 157 |
| 123N-48 | 101 |

The above results clearly demonstrate the presence of increased lysophospholipase activity in supernatants.

Expression and Secretion of C-terminal Deleted LLPL-2 Gene in *Aspergillus oryzae*

LLPL-2 with the C-terminal deleted (LLPL-2-CD) was made from genomic DNA of a strain of *A. niger* by PCR with the primers HU219 (SEQ ID NO: 17) and HU244 (SEQ ID NO: 18), which included an EagIand a PmeI restriction enzyme site, respectively.

Reaction components (1 ng/ml of genomic DNA, 250 mM dNTP each, primer 250 nM each, 0.1 U/ml in Taq polymerase in 1×buffer (Roche Diagnostics, Japan)) were mixed and submitted for PCR under the following conditions.

| Step | Temperature | time |
|---|---|---|
| 1 | 94° C. | 2 min |
| 2 | 92° C. | 1 min |

-continued

| Step | Temperature | time |
|---|---|---|
| 3 | 55° C. | 1 min |
| 4 | 72° C. | 1.5 min |
| 5 | 72° C. | 10 min |
| 6 | 4° C. | forever |

Step 2 to 4 were repeated 30 times.

The 1.3 kb fragment was digested with EagI and PmeI and ligated into the EagIand PmeI sites in the pLLPL-2 having LLPL-2 gene with Ligation high.(TOYOBO). The ligation mixture was transformed into *E. coli* JM109. The resultant plasmid (pHUda126) was sequenced to confirm that nucleotides 115–1824 of SEQ ID NO: 3 were intact and that nucleotides 1825–1914 of SEQ ID NO: 3 had been deleted, corresponding to a C-terminal deletion of amino acids S571-L600 of LLPL-2 (SEQ ID NO: 4).

The 2.0 kb fragment encoding LLPL-2-CD was obtained by digesting pHUda126 with BglII and SmaI. The 2.0 kb fragment was gel-purified with the QIA gel extraction kit and ligated into the BamHI and NurI sites in the Aspergillus expression cassette pCaHj483 with Ligation high. The ligation mixture was transformed into *E. coli* JM109.

The resultant plasmid (pHUda128) for LLPL-2-CD expression cassette was constructed and transformed into the *A. oryzae* strain, BECh-2. Selected transformants were inoculated in 100 ml of MS-9 media and cultivated at 30° C. for 1 day. 3 ml of grown cell in MS-9 medium was inoculated to 100 ml of MDU-pH5 medium and cultivated cultivated at 30° C. for 3 days.

Supernatant was obtained by centrifugation, and the lysophospholipase activity was measured as described above. The table below shows the lysophospholipase activity from of the selected transformants, relative to the activity of the host strain, BECh-2 which was normalized to 1.0.

| Strain | Yield (supernatant) Relative activity |
|---|---|
| BECh-2 | 1.0 |
| 128-3 | 9 |
| 128-9 | 7 |
| 128-12 | 33 |
| 128-15 | 11 |

The above results clearly demonstrate the presence of increased lysophospholipase activity in supernatants.

Example 7

Use of *A. niger* LLPL-2 in Filtration

Filtration performance was determined at 60° C. and pH 4.5 using partially hydrolyzed wheat starch, as follows: The wheat starch hydrolyzate (25 ml in a 100 ml flask) was mixed with LLPL-2 from Example 4 at a dosage of 0.4 L/t dry matter and incubated 6 hours at 60° C. under magnetic stirring. A control was made without enzyme addition. After 6 hours incubation the hydrolyzate was decanted into a glass and left to settle for 10 min at room temperature. The tendency of the sample to flocculate was determined by visual inspection and ranged as excellent, good, fair, bad, or none. The filtration flux was subsequently determined by running the sample through a filter (Whatman no. 4) and measuring the amount of filtrate after 2, 5, and 10 min. The clarity of the filtered sample was measured spectrophotometrically at 720 nm. The flux of filtrate (ml) was as follows:

| Time | Control | LLPL-2 |
|---|---|---|
| 2 min. | 4 | 8 |
| 5 min. | 8 | 13 |
| 10 min. | 12 | 16 |

These results indicate that LLPL-2 showed a clear effect on the filtration flux compared to a control sample. Furthermore a clear filtrate was obtained by treatment with LLPL-2.

What is claimed is:

1. An isolated lysophospholipase comprising:
   a) a polypeptide encoded by a lysophospholipase encoding part of the DNA sequence cloned into a plasmid present in *Escherichia coli* deposit number DSM 13004;
   b) a polypeptide having an amino acid sequence of amino acids 1–600 in SEQ ID NO: 4;
   c) an analogue of the polypeptide defined in (a) or (b) which has at least 95% sequence homology with said polypeptide; or
   d) a polypeptide which is encoded by a nucleic acid sequence which hybridizes with a complementary strand of the nucleic acid sequence shown as nucleotides 115–1914 of SEQ ID NO: 3 under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 65° C.

2. The lysophospholipase of claim 1 which is native to a strain of Aspergillus.

3. The lysophospholipase of claim 2, which is native to a strain of *A. niger*.

4. The lysophospholipase of claim 1, comprising a deletion of 25–35 amino acids at the C-terminal end.

5. The lysophospholipase of claim 1, comprising a polypeptide that is encoded by a nucleic acid sequence which hybridizes with a complementary strand of the nucleic acid sequence shown as nucleotides 115–1914 of SEQ ID NO: 3 under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 65° C.

6. The lysophospholipase of claim 1, comprising a polypeptide that is encoded by a nucleic acid sequence which hybridizes with a complementary strand of the nucleic acid sequence shown as nucleotides 115–1914 of SEQ ID NO: 3 under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 70° C.

7. The lysophospholipase of claim 1, comprising a polypeptide that is encoded by a nucleic acid sequence which hybridizes with a complementary strand of the nucleic acid sequence shown as nucleotides 115–1914 of SEQ ID NO: 3 under hybridization conditions comprising prehybridizing in a solution of 5×SSC, 5×Denhardt's solution, 0.5% SDS and 100 µg/ml of denatured sonicated salmon sperm DNA, followed by hybridization in the same solution for 12 hours at approx. 45° C., followed by washing in 2×SSC, 0.5% SDS for 30 minutes at a temperature of at least 75° C.

8. The lysophospholipase of claim 1, comprising a polypeptide encoded by a lysophospholipase encoding part of the DNA sequence cloned into a plasmid present in *Echerichia coli* deposit number DSM 13004.

9. The lysophospholipase of claim 1, comprising a polypeptide having an amino acid sequence comprising amino acids 1–600 in SEQ ID NO: 4.

10. A process for hydrolyzing fatty acyl groups in a phospholipid or lysophospholipid, comprising treating the phospholipid or lysophospholipid with the lysophospholipase of claim 1.

11. A process for improving the filterability of an aqueous solution or slurry of carbohydrate origin which contains phospholipid, which process comprises treating the solution or slurry with the lysophospholipase of claim 1.

12. The process of claim 11 wherein the solution or slurry contains a starch hydrolysate.

13. The process of claim 11, wherein the solution or slurry contains a wheat starch hydrolysate.

* * * * *